(12) United States Patent
Hernandez-Rosas et al.

(10) Patent No.: US 12,396,663 B2
(45) Date of Patent: Aug. 26, 2025

(54) SYSTEMS AND METHODS FOR MONITORING AND MANAGING LIFE OF A BATTERY IN AN ANALYTE SENSOR SYSTEM WORN BY A USER

(71) Applicant: Dexcom, Inc., San Diego, CA (US)

(72) Inventors: Jose Hector Hernandez-Rosas, San Diego, CA (US); Mark Dervaes, Carlsbad, CA (US); Peter C. Simpson, Cardiff, CA (US); Apurv Ullas Kamath, San Diego, CA (US); Tom Miller, Valley Center, CA (US); Shawn Larvenz, Ramona, CA (US); Stephen J. Vanslyke, Carlsbad, CA (US)

(73) Assignee: Dexcom, Inc., San Diego, CA (US)

( * ) Notice: Subject to any disclaimer, the term of this patent is extended or adjusted under 35 U.S.C. 154(b) by 37 days.

(21) Appl. No.: 18/337,564

(22) Filed: Jun. 20, 2023

(65) Prior Publication Data

US 2023/0329595 A1    Oct. 19, 2023

Related U.S. Application Data

(63) Continuation of application No. 16/442,309, filed on Jun. 14, 2019, now Pat. No. 11,690,538, which is a
(Continued)

(51) Int. Cl.
*A61B 5/145*   (2006.01)
*A61B 5/00*    (2006.01)
*H04W 52/02*   (2009.01)

(52) U.S. Cl.
CPC ........ *A61B 5/14532* (2013.01); *A61B 5/0004* (2013.01); *A61B 5/002* (2013.01);
(Continued)

(58) Field of Classification Search
CPC ... A61B 5/14532; A61B 5/0004; A61B 5/002; A61B 5/0022; A61B 5/14546;
(Continued)

(56) References Cited

U.S. PATENT DOCUMENTS 7,310,544 B2   12/2007   Brister et al.
7,430,675 B2    9/2008   Lee
(Continued)

FOREIGN PATENT DOCUMENTS

CN   101051045 A   10/2007
CN   101461197 A    6/2009
(Continued)

OTHER PUBLICATIONS

International Preliminary Report on Patentability for Application No. PCT/US2014/070104 mailed on Jun. 30, 2016, 10 pages.
(Continued)

*Primary Examiner* — Eric J Messersmith
(74) *Attorney, Agent, or Firm* — Patterson + Sheridan, LLP

(57) ABSTRACT

Systems and methods for analyte monitoring, particularly systems and methods for monitoring and managing life of a battery in an analyte sensor system worn by a user, are provided.

20 Claims, 11 Drawing Sheets

Related U.S. Application Data continuation of application No. 14/974,865, filed on Dec. 18, 2015, now Pat. No. 10,362,973, which is a continuation of application No. 14/569,512, filed on Dec. 12, 2014, now Pat. No. 10,052,050.

(60) Provisional application No. 61/916,778, filed on Dec. 16, 2013.

(52) U.S. Cl.
CPC ........ *A61B 5/0022* (2013.01); *A61B 5/14546* (2013.01); *A61B 5/6802* (2013.01); *A61B 5/7282* (2013.01); *A61B 5/742* (2013.01); *A61B 5/7475* (2013.01); *H04W 52/0277* (2013.01); *A61B 2560/0204* (2013.01); *A61B 2560/0209* (2013.01); *A61B 2560/0214* (2013.01); *Y02D 30/70* (2020.08)

(58) Field of Classification Search
CPC ..... A61B 5/6802; A61B 5/7282; A61B 5/742; A61B 5/7475; A61B 2560/0204; A61B 2560/0209; A61B 2560/0214; H04W 52/0277; Y02D 30/70
See application file for complete search history.

(56) References Cited

U.S. PATENT DOCUMENTS

| | | | |
|---|---|---|---|
| 8,588,882 B2 | 11/2013 | Kamath et al. | |
| 8,963,773 B2 | 2/2015 | Van Diggelen et al. | |
| 8,993,331 B2 | 3/2015 | Nekoomaram et al. | |
| 9,144,204 B2 | 9/2015 | Redmond et al. | |
| 9,196,139 B2 | 11/2015 | Gutierrez et al. | |
| 9,241,631 B2 | 1/2016 | Valdes et al. | |
| 9,566,450 B2 | 2/2017 | Joglekar et al. | |
| 9,830,670 B2 | 11/2017 | Fadell | |
| 10,052,050 B2 | 8/2018 | Hernandez-Rosas et al. | |
| 10,362,973 B2 | 7/2019 | Hernandez-Rosas et al. | |
| 2004/0048589 A1 | 3/2004 | Yamamoto et al. | |
| 2006/0161212 A1 | 7/2006 | Rasch-Menges et al. | |
| 2008/0201587 A1 | 8/2008 | Lee | |
| 2009/0275354 A1 | 11/2009 | Bulmer | |
| 2010/0010857 A1 | 1/2010 | Fadell | |
| 2010/0174167 A1 | 7/2010 | Kamath et al. | |
| 2010/0207585 A1 | 8/2010 | Duvalsaint et al. | |
| 2010/0312744 A1* | 12/2010 | Prokhorov | G01R 31/392 706/15 |
| 2011/0054282 A1* | 3/2011 | Nekoomaram | G01K 13/00 600/347 |
| 2011/0172939 A1* | 7/2011 | Uprety | G01R 31/389 702/63 |
| 2011/0263958 A1 | 10/2011 | Brauker et al. | |
| 2012/0108934 A1 | 5/2012 | Valdes et al. | |
| 2012/0109260 A1 | 5/2012 | Stancer et al. | |
| 2012/0161959 A1 | 6/2012 | Palmer et al. | |
| 2012/0185188 A1* | 7/2012 | Wang | G01R 31/389 702/63 |
| 2012/0215366 A1* | 8/2012 | Redmond | G05B 19/042 700/284 |
| 2014/0073262 A1 | 3/2014 | Gutierrez et al. | |
| 2015/0077126 A1 | 3/2015 | Wang et al. | |
| 2015/0119846 A1 | 4/2015 | Joglekar et al. | |
| 2015/0164404 A1 | 6/2015 | Euliano et al. | |
| 2019/0307376 A1 | 10/2019 | Hernandez-Rosas et al. | |

FOREIGN PATENT DOCUMENTS

| | | |
|---|---|---|
| CN | 102113034 A | 6/2011 |
| CN | 102316795 A | 1/2012 |
| CN | 102542765 A | 7/2012 |
| CN | 102905928 A | 1/2013 |
| CN | 103376414 A | 10/2013 |
| EP | 1997435 A1 | 12/2008 |
| EP | 2174592 A1 | 4/2010 |
| JP | 2010206596 A | 9/2010 |
| WO | 2011026148 A1 | 3/2011 |
| WO | 2013144617 A1 | 10/2013 |

OTHER PUBLICATIONS

International Search Report and Written Opinion for Application No. PCT/US2014/070104 mailed May 12, 2015, 14 pages.

* cited by examiner

SYSTEMS AND METHODS FOR MONITORING AND MANAGING LIFE OF A BATTERY IN AN ANALYTE SENSOR SYSTEM WORN BY A USER

CROSS-REFERENCE TO RELATED APPLICATIONS

This application is a continuation of U.S. patent application Ser. No. 16/442,309, filed Jun. 14, 2019, which is a continuation of U.S. patent application Ser. No. 14/974,865, filed Dec. 18, 2015, now issued as U.S. Pat. No. 10,362,973, which is a continuation of U.S. patent application Ser. No. 14/569,512, filed Dec. 12, 2014, now issued as U.S. Pat. No. 10,052,050, which claims the benefit of U.S. Provisional Patent Application No. 61/916,778, filed Dec. 16, 2013. The aforementioned applications are incorporated by reference herein in their entirety, and are hereby expressly made a part of this specification.

FIELD

Systems and methods for analyte monitoring, particularly systems and methods for monitoring and managing life of a battery in an analyte sensor system worn by a user, are provided.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically requires uncomfortable finger pricking methods. Due to the lack of comfort and convenience, a diabetic will normally only measure his or her glucose level two to four times per day. Unfortunately, these time intervals are spread so far apart that the diabetic will likely find out too late, sometimes incurring dangerous side effects, of a hyperglycemic or hypoglycemic condition. In fact, it is not only unlikely that a diabetic will take a timely SMBG value, but additionally the diabetic will not know if his blood glucose value is going up (higher) or down (lower) based on conventional methods.

Consequently, a variety of non-invasive, transdermal (e.g., transcutaneous) and/or implantable electrochemical sensors are being developed for continuously detecting and/or quantifying blood glucose values. These devices generally transmit raw or minimally processed data for subsequent analysis at a remote device, which can include a display.

SUMMARY

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

In a first aspect, a method for monitoring a battery installed in an analyte sensor system worn by a user is provided. The method can comprise measuring a value indicative of a current power level of the battery; and predicting remaining useful life of the battery based on the measured value indicative of the current power level and an assumed future usage of the analyte sensor system.

In certain implementations of the first aspect, which is generally applicable, particularly with any other implementation of the first aspect, the method can further comprise In certain implementations of the first aspect, which is generally applicable, particularly with any other implementation of the first aspect, the analyte sensor system can be a continuous glucose sensor system.

In certain implementations of the first aspect, which is generally applicable, particularly with any other implementation of the first aspect, the measured value can be a voltage drop indicative of an internal resistance of the battery.

In certain implementations of the first aspect, which is generally applicable, particularly with any other implementation of the first aspect, the method can further comprise comparing the voltage drop to a predetermined voltage profile curve associated with the battery.

In certain implementations of the first aspect, which is generally applicable, particularly with any other implementation of the first aspect, the voltage drop can be measured while the battery is connected to an artificial load consisting of one or more passive components.

In certain implementations of the first aspect, which is generally applicable, particularly with any other implementation of the first aspect, the voltage drop can be measured while the battery is connected to an artificial load comprising an active component configured as a constant current source.

In certain implementations of the first aspect, which is generally applicable, particularly with any other implementation of the first aspect, the voltage drop can be measured while the analyte sensor system performs one or more tasks known to draw a constant current from the battery.

In certain implementations of the first aspect, which is generally applicable, particularly with any other implementation of the first aspect, the one or more tasks can include a specific wireless transmission mode.

In certain implementations of the first aspect, which is generally applicable, particularly with any other implementation of the first aspect, the specific wireless transmission mode can be used for a bulk transfer of data items stored in a database.

In certain implementations of the first aspect, which is generally applicable, particularly with any other implementation of the first aspect, the measured value can be an output of a Coulomb counter configured to provide an integral of a load current drawn from the battery over time.

In certain implementations of the first aspect, which is generally applicable, particularly with any other implementation of the first aspect, the measured value can be a number of event counts associated with usage of the analyte sensor system.

In certain implementations of the first aspect, which is generally applicable, particularly with any other implementation of the first aspect, the method can further comprise incrementing the number of event counts based on number and type of transactions performed by the analyte sensor system.

In certain implementations of the first aspect, which is generally applicable, particularly with any other implementation of the first aspect, the transactions can include a regularly-scheduled transmission of a current measured analyte value and a bulk transfer of stored past measured analyte values, and the bulk transfer causes a greater increment in the number of events as compared to the regularly-scheduled transmission.

In certain implementations of the first aspect, which is generally applicable, particularly with any other implementation of the first aspect, the number of event counts can include a time count indicative of time elapsed since the battery was installed in the analyte sensor system.

In certain implementations of the first aspect, which is generally applicable, particularly with any other implementation of the first aspect, the elapsed time can include time the analyte sensor system was on a shelf prior to first usage.

In certain implementations of the first aspect, which is generally applicable, particularly with any other implementation of the first aspect, wherein the measured value can be a number of counts, the number of counts being a sum of a time count indicative of time the analyte sensor system was on a shelf prior to first usage and a number of event counts associated with usage of the analyte sensor system.

In certain implementations of the first aspect, which is generally applicable, particularly with any other implementation of the first aspect, the assumed future usage can be based on stored history of prior usage of the analyte sensor system.

In certain implementations of the first aspect, which is generally applicable, particularly with any other implementation of the first aspect, the method can further comprise transmitting data indicative of the current power level of the battery to a display device configured to display analyte values received from the analyte sensor system.

In certain implementations of the first aspect, which is generally applicable, particularly with any other implementation of the first aspect, the method can further comprise transmitting an alert indicating that the current power level of the battery is less than a predefined power level a display device configured to display analyte values received from the analyte sensor system.

In certain implementations of the first aspect, which is generally applicable, particularly with any other implementation of the first aspect, the method can further comprise transmitting data indicative of the predicted remaining useful life of the battery to a display device configured to display analyte values received from the analyte sensor system.

In certain implementations of the first aspect, which is generally applicable, particularly with any other implementation of the first aspect, the method can further comprise transmitting a first alert indicating that the predicted remaining useful life is less than a predefined time to a display device configured to display analyte values received from the analyte sensor system.

In certain implementations of the first aspect, which is generally applicable, particularly with any other implementation of the first aspect, the method can further comprise disabling one or more functions of the analyte sensor system after passage of the predicted remaining useful life.

In certain implementations of the first aspect, which is generally applicable, particularly with any other implementation of the first aspect, the method can further comprise transmitting a second alert indicating that one or more functions of the analyte sensor system have been disabled.

In a second aspect, an analyte sensor system worn by a user is provided. The analyte sensor system can comprise an analyte sensor; a transceiver configured to transmit and receive wireless signals; a battery; a battery measurement module coupled to the battery and configured to measure a value indicative of a current power level of the battery; a prediction module coupled to the battery measurement module and configured to predict remaining useful life of the battery based on the measured value and an assumed future usage of the analyte sensor system; and a control module coupled to the transceiver and at least one of the battery measurement module and the prediction module and configured to control one or more data transmission functions of the analyte sensor system based on at least one of the measured value and the predicted remaining useful life.

In certain implementations of the second aspect, which is generally applicable, particularly with any other implementation of the second aspect, the analyte sensor system can be a continuous glucose sensor system.

In certain implementations of the second aspect, which is generally applicable, particularly with any other implementation of the second aspect, the battery measurement module can include a voltage sensor configured to measure a voltage drop indicative of an internal resistance of the battery.

In certain implementations of the second aspect, which is generally applicable, particularly with any other implementation of the second aspect, the analyte sensor system can further comprise a memory configured to store a predetermined voltage profile curve associated with the battery, and a comparison module configured to compare the measured voltage drop to the voltage profile curve, and determine the current power level based on the comparison.

In certain implementations of the second aspect, which is generally applicable, particularly with any other implementation of the second aspect, the battery measurement module can measure the voltage drop while the battery is connected to an artificial load.

In certain implementations of the second aspect, which is generally applicable, particularly with any other implementation of the second aspect, the artificial load can comprise an active component configured to act as a constant current source.

In certain implementations of the second aspect, which is generally applicable, particularly with any other implementation of the second aspect, the active component can include an operational amplifier.

In certain implementations of the second aspect, which is generally applicable, particularly with any other implementation of the second aspect, the active component can include a MOSFET.

In certain implementations of the second aspect, which is generally applicable, particularly with any other implementation of the second aspect, the battery measurement module can measure the voltage drop while the analyte sensor system performs one or more tasks known to draw a constant current from the battery.

In certain implementations of the second aspect, which is generally applicable, particularly with any other implementation of the second aspect, the one or more tasks can include a specific wireless transmission mode.

In certain implementations of the second aspect, which is generally applicable, particularly with any other implementation of the second aspect, the prediction module can be configured to predict when the voltage drop will exceed a predefined maximum allowed voltage drop.

In certain implementations of the second aspect, which is generally applicable, particularly with any other implementation of the second aspect, the battery measurement module can include a Coulomb counter configured to provide an integral of a current drawn from the battery over time.

In certain implementations of the second aspect, which is generally applicable, particularly with any other implementation of the second aspect, the battery measurement module can include a counter configured to count a number of events associated with usage of the analyte sensor system.

In certain implementations of the second aspect, which is generally applicable, particularly with any other implementation of the second aspect, the counter can be configured to increment the number of events based on number and type of transactions performed by the analyte sensor system.

In certain implementations of the second aspect, which is generally applicable, particularly with any other implementation of the second aspect, the counter can be further configured to increment the number of events based on time elapsed since the battery was first installed in the analyte sensor system.

In certain implementations of the second aspect, which is generally applicable, particularly with any other implementation of the second aspect, the elapsed time can include time the analyte sensor system was on shelf before first usage.

In certain implementations of the second aspect, which is generally applicable, particularly with any other implementation of the second aspect, the assumed future usage can be based on stored history of prior usage of the analyte sensor system.

In certain implementations of the second aspect, which is generally applicable, particularly with any other implementation of the second aspect, the control module can be configured to disable one or more data transmission functions of the analyte sensor system if the current power level of the battery is less than a predefined power level.

In certain implementations of the second aspect, which is generally applicable, particularly with any other implementation of the second aspect, the control module can be configured to disable one or more data transmission functions of the analyte sensor system if the predicted remaining useful life of the battery is less than a predefined time.

In certain implementations of the second aspect, which is generally applicable, particularly with any other implementation of the second aspect, the control module can be configured to cause the transceiver to transmit data indicative of the current power level of the battery to a display device for displaying analyte values received from the transceiver.

In certain implementations of the second aspect, which is generally applicable, particularly with any other implementation of the second aspect, the control module can be configured to cause the transceiver to transmit an alert indicating that the current power level of the battery is less than a predefined power level to a display device for displaying analyte values received from the transceiver.

In certain implementations of the second aspect, which is generally applicable, particularly with any other implementation of the second aspect, the control module can be configured to cause the transceiver to transmit data indicative of the predicted remaining useful life of the battery to a display device for displaying analyte values received from the transceiver.

In certain implementations of the second aspect, which is generally applicable, particularly with any other implementation of the second aspect, the control module can be configured to cause the transceiver to transmit a first alert indicating that the predicted remaining useful life of the battery is less than a predefined time to a display device for displaying analyte values received from the transceiver.

In certain implementations of the second aspect, which is generally applicable, particularly with any other implementation of the second aspect, the control module can be configured to disable one or more functions of the analyte sensor system after passage of the predicted remaining useful life.

In certain implementations of the second aspect, which is generally applicable, particularly with any other implementation of the second aspect, the control module can be configured to cause the transceiver to transmit a second alert indicating that one or more functions of the analyte sensor system have been disabled.

In certain implementations of the second aspect, which is generally applicable, particularly with any other implementation of the second aspect, the one or more disabled functions can include a bulk transfer of stored past measured analyte values.

In certain implementations of the second aspect, which is generally applicable, particularly with any other implementation of the second aspect, the one or more disabled functions include regularly-scheduled transmissions of analyte values.

In a third aspect, a method for prolonging life of a battery installed in an analyte sensor system worn by a user is provided. The method can comprise determining a remaining power level of the battery; determining that the remaining power level of the battery is below a predetermined power level; and altering one or more operations of the analyte sensor system.

In certain implementations of the third aspect, which is generally applicable, particularly with any other implementation of the third aspect, the analyte sensor system can be a continuous glucose sensor system.

In certain implementations of the third aspect, which is generally applicable, particularly with any other implementation of the third aspect, the remaining power level of the battery can be determined based on a measured value indicative of a current power level of the battery.

In certain implementations of the third aspect, which is generally applicable, particularly with any other implementation of the third aspect, the remaining power level of the battery can be determined based on a measured value indicative of a current power level of the battery and an assumed future usage of the analyte sensor system.

In certain implementations of the third aspect, which is generally applicable, particularly with any other implementation of the third aspect, the altering step can include reducing a radio frequency transmission power level of the analyte sensor system.

In certain implementations of the third aspect, which is generally applicable, particularly with any other implementation of the third aspect, the radio frequency transmission power level can be reduced upon a prior determination that the analyte sensor system is in close proximity of the display device.

In certain implementations of the third aspect, which is generally applicable, particularly with any other implementation of the third aspect, the altering step can include limiting bulk transfers of stored past measured analyte values.

In certain implementations of the third aspect, which is generally applicable, particularly with any other implementation of the third aspect, the bulk transfers can be cancelled altogether.

In certain implementations of the third aspect, which is generally applicable, particularly with any other implementation of the third aspect, only part of the stored past measured analyte values can be included in the limited bulk transfers.

In certain implementations of the third aspect, which is generally applicable, particularly with any other implementation of the third aspect, the altering step can include increasing an interval between regularly-scheduled transmissions of analyte values.

In certain implementations of the third aspect, which is generally applicable, particularly with any other implementation of the third aspect, the altering step can include skipping one or more of regularly-scheduled transmissions of analyte values.

In certain implementations of the third aspect, which is generally applicable, particularly with any other implementation of the third aspect, the altering step can include cancelling regularly-scheduled transmissions of analyte values and transmitting an analyte value in response to one or more events instead.

In certain implementations of the third aspect, which is generally applicable, particularly with any other implementation of the third aspect, the one or more events can include a user prompt of data.

In certain implementations of the third aspect, which is generally applicable, particularly with any other implementation of the third aspect, the one or more events can include one or more analyte values exceeding or falling below a threshold analyte value.

In a fourth aspect, an analyte sensor system worn by a user is provided. The analyte sensor system can include an analyte sensor; a transceiver configured to transmit and receive wireless signals; a battery; and a control module coupled to the transceiver and configured to: determine that a remaining power level of the battery is below a predefined power level, and cause a change in one or more data transmission operations of the analyte sensor system.

In certain implementations of the fourth aspect, which is generally applicable, particularly with any other implementation of the fourth aspect, the analyte sensor system can be a continuous glucose sensor system.

In certain implementations of the fourth aspect, which is generally applicable, particularly with any other implementation of the fourth aspect, the analyte sensor system can further comprise a battery measurement module configured to measure a value indicative of a current power level of the battery and a prediction module configured to predict the remaining useful life of the battery based on the measured value.

In certain implementations of the fourth aspect, which is generally applicable, particularly with any other implementation of the fourth aspect, the analyte sensor system can further comprise a battery measurement module configured to measure a value indicative of a current power level of the battery and a prediction module configured to predict the remaining useful life of the battery based on the measured value and an assumed future usage of the analyte sensor system.

In certain implementations of the fourth aspect, which is generally applicable, particularly with any other implementation of the fourth aspect, the change includes a reduction in a radio frequency transmission power level of the transceiver.

In certain implementations of the fourth aspect, which is generally applicable, particularly with any other implementation of the fourth aspect, the reduction in the radio frequency transmission power level of the transceiver can be preceded by a determination that the analyte sensor system is in close proximity of a display device for displaying analyte values received from the transceiver.

In certain implementations of the fourth aspect, which is generally applicable, particularly with any other implementation of the fourth aspect, the change can include a limitation on bulk transfers of past measured analyte values stored at the analyte sensor system.

In certain implementations of the fourth aspect, which is generally applicable, particularly with any other implementation of the fourth aspect, the limitation can include a cancellation of the bulk transfers altogether.

In certain implementations of the fourth aspect, which is generally applicable, particularly with any other implementation of the fourth aspect, the limitation can include a transfer of only part of the stored past measured analyte values in the bulk transfers.

In certain implementations of the fourth aspect, which is generally applicable, particularly with any other implementation of the fourth aspect, the change can include an increase in an interval between regularly-scheduled transmissions of analyte values.

In certain implementations of the fourth aspect, which is generally applicable, particularly with any other implementation of the fourth aspect, the change can include skipping one or more of regularly-scheduled transmissions of analyte values.

In certain implementations of the fourth aspect, which is generally applicable, particularly with any other implementation of the fourth aspect, the change can include a cancellation of regularly scheduled transmissions of analyte values and a transmission of an analyte value in response to one or more events instead.

In certain implementations of the fourth aspect, which is generally applicable, particularly with any other implementation of the fourth aspect, the one or more events can include a user prompt of data.

In certain implementations of the fourth aspect, which is generally applicable, particularly with any other implementation of the fourth aspect, the one or more events can include analyte values exceeding or falling below a threshold analyte value.

In a fifth aspect, a method for prolonging life of a battery installed in an analyte sensor system worn by a user is provided. The method can include measuring a first analyte value at a first time; causing a transmission of the measured first analyte value along with a predicted second analyte value; measuring a second analyte value at a second time; determining whether a difference between the measured second analyte value and the predicted second analyte value is within a predefined range; and skipping a transmission of the measured second analyte value if the difference is within the predefined range.

In certain implementations of the fifth aspect, which is generally applicable, particularly with any other implementation of the fifth aspect, the analyte sensor system can be a continuous glucose sensor system.

In certain implementations of the fifth aspect, which is generally applicable, particularly with any other implementation of the fifth aspect, at least one additional predicted future analyte value can be transmitted along with the measured first analyte value and the predicted second analyte value and the method can further comprise skipping transmission of at least one additional measured future analyte values if a difference between the at least one additional measured future analyte value and the at least one additional predicted future analyte values is within the predetermined range.

In certain implementations of the fifth aspect, which is generally applicable, particularly with any other implementation of the fifth aspect, the predefined range can be variable depending on at least one of a current analyte value a predicted analyte value.

In certain implementations of the fifth aspect, which is generally applicable, particularly with any other implementation of the fifth aspect, the variable predefined range can be determined based at least partly on a clinical error grid associated with the analyte being measured.

In a sixth aspect, an analyte sensor system worn by a user is provided. The analyte sensor system can comprise an analyte sensor; a sensor measurement module coupled to the analyte sensor and configured to provide measured analyte values; a transceiver configured to transmit and receive wireless signals to and from a display device configured to display measured analyte values; a battery; a control module coupled to the sensor measurement module and the transceiver and configured to: receive a measured first analyte value at a first time, cause a transmission of the measured first analyte value to the display device along with a predicted second analyte value, receive a measured second analyte value from the sensor measurement module at a second time; determine whether a difference between the measured second analyte value and the predicted second analyte value is within a predefined range; and skip a transmission of the measured second analyte value if the difference is within the predefined range.

In certain implementations of the sixth aspect, which is generally applicable, particularly with any other implementation of the sixth aspect, the analyte sensor system can be a continuous glucose sensor system.

In certain implementations of the sixth aspect, which is generally applicable, particularly with any other implementation of the sixth aspect, the control module can be further configured to cause the transceiver to transmit at least one additional predicted future analyte value along with the measured first analyte value and the predicted second analyte value, and cause the transmitter to skip transmission of at least one additional measured future analyte values if a difference between the at least one additional measured future analyte value and the at least one additional predicted future analyte values is within the predetermined range.

In certain implementations of the sixth aspect, which is generally applicable, particularly with any other implementation of the sixth aspect, the predefined range can be variable depending on at least one of a current measured analyte value and a predicted future analyte value.

In certain implementations of the sixth aspect, which is generally applicable, particularly with any other implementation of the sixth aspect, the variable predefined range can be determined based at least partly on a clinical error grid associated with the analyte being measured.

Any of the features of aspects specified herein are applicable to all other aspects and embodiments identified herein. Moreover, any of the features of an aspect is independently combinable, partly or wholly with other aspects described herein in any way, e.g., one, two, or three or more aspects may be combinable in whole or in part. Further, any of the features of an aspect may be made optional to other aspects. Any aspect of a method can be performed by a system or apparatus of another aspect, and any aspect or of a system can be configured to perform a method of another aspect.

DETAILED DESCRIPTION

Figure 1:
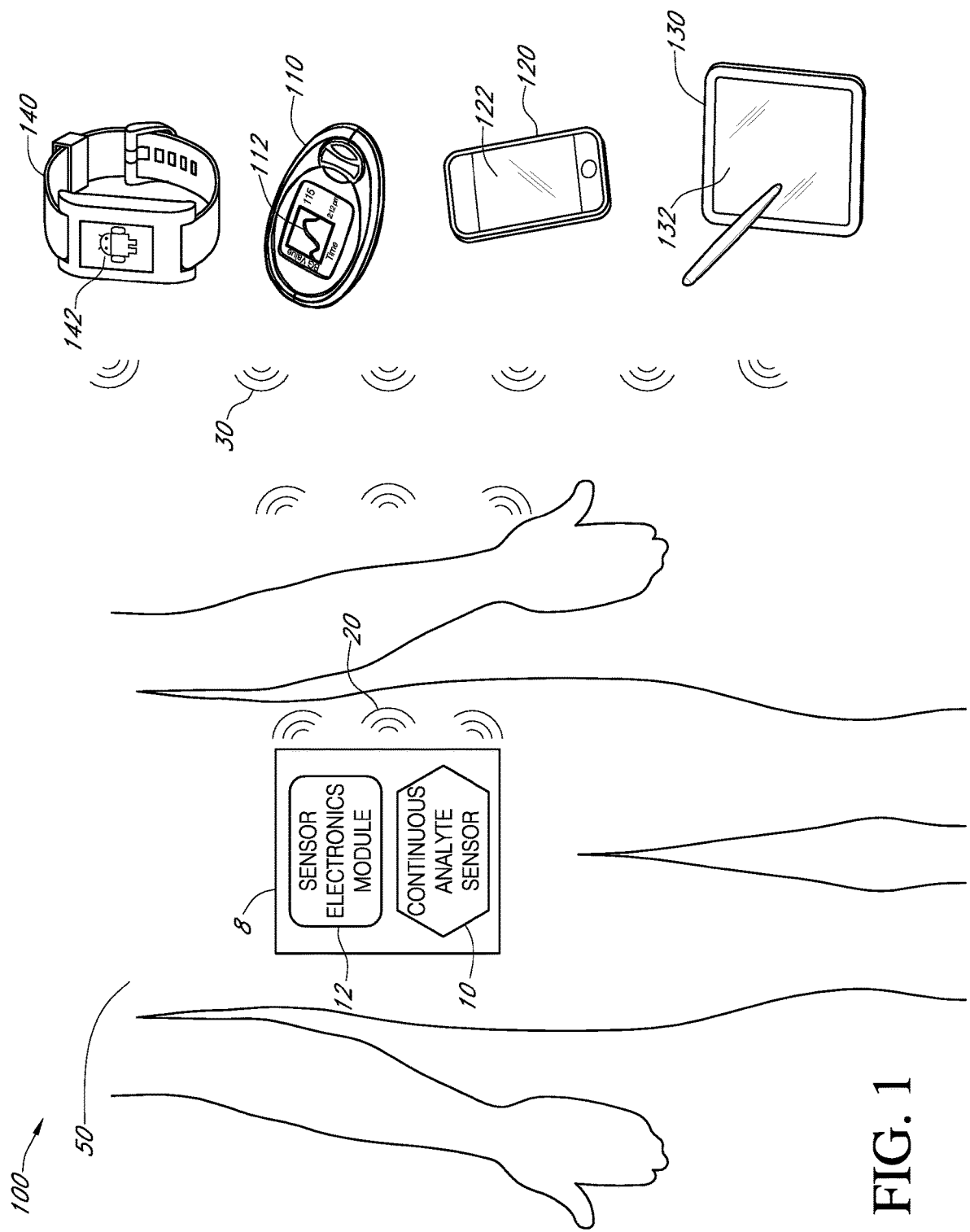
FIG. 1 is a diagram illustrating certain embodiments of a continuous analyte sensor system according certain aspects of the present disclosure.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Overview

In some embodiments, a system is provided for continuous measurement of an analyte in a host that includes: a continuous analyte sensor configured to continuously measure a concentration of the analyte in the host and a sensor electronics module physically connected to the continuous analyte sensor during sensor use. In certain embodiments, the sensor electronics module includes electronics configured to process a data stream associated with an analyte concentration measured by the continuous analyte sensor in order to generate sensor information that includes raw sensor data, transformed sensor data, and/or any other sensor data, for example. The sensor electronics module may further be configured to generate sensor information that is customized for respective display devices, such that different display devices may receive different sensor information.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is analyte. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica,* enterovirus, *Giardia duodenalisa, Helicobacter pylori,* hepatitis B virus, herpes virus, HIV-1, IgE (atopic disease), influenza virus, *Leishmania donovani,* leptospira, measles/mumps/rubella, *Mycobacterium leprae, Mycoplasma pneumoniae,* Myoglobin, *Onchocerca volvulus,* parainfluenza virus, *Plasmodium falciparum,* poliovirus, *Pseudomonas aeruginosa,* respiratory syncytial virus, *rickettsia* (scrub typhus), *Schistosoma mansoni, Toxoplasma gondii, Trepenoma pallidium, Trypanosoma cruzi/rangeli,* vesicular *stomatis* virus, *Wuchereria bancrofti,* yellow fever virus); specific antigens (hepatitis B virus, HIV-1); succinylacetone; sulfadoxine; theophylline; thyrotropin (TSH); thyroxine (T4); thyroxine-binding globulin; trace elements; transferring; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

Alerts

In certain embodiments, one or more alerts are associated with an analyte monitoring system. For example, each alert may include one or more alert conditions that indicate when the respective alert has been triggered. For example, a hypoglycemic alert may include alert conditions indicating a minimum glucose level. The alert conditions may also be based on transformed sensor data, such as trending data, and/or sensor data from multiple different sensors (e.g. an alert may be based on sensor data from both a glucose sensor and a temperature sensor). For example, a hypoglycemic alert may include alert conditions indicating a minimum required trend in the host's glucose level that must be present before triggering the alert. The term "trend," as used herein refers generally to data indicating some attribute of data that is acquired over time, e.g., such as calibrated or filtered data from a continuous glucose sensor. A trend may indicate amplitude, rate of change, acceleration, direction, etc., of data, such as sensor data, including transformed or raw sensor data.

In certain embodiments, each of the alerts is associated with one or more actions that are to be performed in response to triggering of the alert. Alert actions may include, for example, activating an alarm, such as displaying information on a display of the sensor electronics module or activating an audible or vibratory alarm coupled to the sensor electronics module, and/or transmitting data to one or more display devices external to the sensor electronics module. For any delivery action that is associated with a triggered alert, one or more delivery options define the content and/or format of the data to be transmitted, the device to which the data is to be transmitted, when the data is to be transmitted, and/or a communication protocol for delivery of the data.

In certain embodiments, multiple delivery actions (each having respective delivery options) may be associated with a single alert such that displayable sensor information having different content and formatting, for example, is transmitted to respective display devices in response to triggering of a single alert. For example, a mobile telephone may receive a data package including minimal displayable sensor information (that may be formatted specifically for display on the mobile telephone), while a desktop computer may receive a data package including most (or all) of the displayable sensor information that is generated by the sensor electronics module in response to triggering of a common alert. Advantageously, the sensor electronics module is not tied to a single display device, rather it is configured to communicate with a plurality of different display devices directly, systematically, simultaneously (e.g., via broadcasting), regularly, periodically, randomly, on-demand, in response to a query, based on alerts or alarms, and/or the like.

In some embodiments, clinical risk alerts are provided that include alert conditions that combine intelligent and dynamic estimative algorithms that estimate present or predicted danger with greater accuracy, more timeliness in pending danger, avoidance of false alarms, and less annoyance for the patient. In general, clinical risk alerts include dynamic and intelligent estimative algorithms based on analyte value, rate of change, acceleration, clinical risk, statistical probabilities, known physiological constraints, and/or individual physiological patterns, thereby providing more appropriate, clinically safe, and patient-friendly alarms. U.S. Patent Publication No. US-2007-0208246-A1, which is incorporated herein by reference in its entirety, describes some systems and methods associated with the clinical risk alerts (or alarms) described herein. In some embodiments, clinical risk alerts can be triggered for a predetermined time period to allow for the user to attend to his/her condition. Additionally, the clinical risk alerts can be de-activated when leaving a clinical risk zone so as not to annoy the patient by repeated clinical alarms (e.g., visual, audible or vibratory), when the patient's condition is improving. In some embodiments, dynamic and intelligent estimation determines a possibility of the patient avoiding clinical risk, based on the analyte concentration, the rate of change, and other aspects of the dynamic and intelligent estimative algorithms. If there is minimal or no possibility of avoiding the clinical risk, a clinical risk alert will be triggered. However, if there is a possibility of avoiding the clinical risk, the system is configured to wait a predetermined amount of time and re-analyze the possibility of avoiding the clinical risk. In some embodiments, when there is a possibility of avoiding the clinical risk, the system is further configured to provide targets, therapy recommendations, or other information that can aid the patient in proactively avoiding the clinical risk.

In some embodiments, the sensor electronics module is configured to search for one or more display devices within communication range of the sensor electronics module and to wirelessly communicate sensor information (e.g., a data package including displayable sensor information, one or more alarm conditions, and/or other alarm information) thereto. Accordingly, the display device is configured to display at least some of the sensor information and/or alarm the host (and/or care taker), wherein the alarm mechanism is located on the display device.

In some embodiments, the sensor electronics module is configured to provide one or a plurality of different alarms via the sensor electronics module and/or via transmission of a data package indicating an alarm should be initiated by one or a plurality of display devices (e.g., sequentially and/or simultaneously). In some embodiments, the sensor electronics module is configured to provide sensor data (e.g., analyte values) to the display device and the display device triggers alerts based on comparison of the sensor data with predefined alert thresholds. In certain embodiments, the sensor electronics module merely provides a data field indicating that an alarm conditions exists and the display device, upon reading the data field indicating the existence of the alarm condition, may decide to trigger an alarm. In some embodiments, the sensor electronics module determines which of the one or more alarms to trigger based on one or more alerts that are triggered. For example, when an alert trigger indicates severe hypoglycemia, the sensor electronics module can perform multiple actions, such as activating an alarm on the sensor electronics module, transmitting a data package to a monitoring device indicating activation of an alarm on the display, and transmitting a data package as a text message to a care provider. As an example, a text message can appear on a custom monitoring device, cell phone, pager device, and/or the like, including displayable sensor information that indicates the host's condition (e.g., "severe hypoglycemia").

In some embodiments, the sensor electronics module is configured to wait a time period for the host to respond to a triggered alert (e.g., by pressing or selecting a snooze and/or off function and/or button on the sensor electronics module and/or a display device), after which additional alerts are triggered (e.g., in an escalating manner) until one or more alerts are responded to. In some embodiments, the sensor electronics module is configured to send control signals (e.g., a stop signal) to a medical device associated with an alarm condition (e.g., hypoglycemia), such as an insulin pump, wherein the stop alert triggers a stop of insulin delivery via the pump.

In some embodiments, the sensor electronics module is configured to directly, systematically, simultaneously (e.g., via broadcasting), regularly, periodically, randomly, on-demand, in response to a query (from the display device), based on alerts or alarms, and/or the like transmit alarm information. In some embodiments, the system further includes a repeater such that the wireless communication distance of the sensor electronics module can be increased, for example, to 10, 20, 30, 50 75, 100, 150, or 200 meters or more, wherein the repeater is configured to repeat a wireless communication from the sensor electronics module to the display device located remotely from the sensor electronics module. A repeater can be useful to families having children with diabetes. For example, to allow a parent to carry, or place in a stationary position, a display device, such as in a large house wherein the parents sleep at a distance from the child.

Display Devices

In some embodiments, the sensor electronics module is configured to search for and/or attempt wireless communication with a display device from a list of display devices. In some embodiments, the sensor electronics module is configured to search for and/or attempt wireless communication with a list of display devices in a predetermined and/or programmable order (e.g., grading and/or escalating), for example, wherein a failed attempt at communication with and/or alarming with a first display device triggers an attempt at communication with and/or alarming with a second display device, and so on. In one exemplary embodiment, the sensor electronics module is configured to search for and attempt to alarm a host or care provider sequentially using a list of display devices, such as: 1) a default display device or a custom analyte monitoring device, 2) a mobile phone via auditory and/or visual methods, such as, text message to the host and/or care provider, voice message to the host and/or care provider, and/or 911), 3) a tablet, 4) a smart watch.

Depending on the embodiment, one or more display devices that receive data packages from the sensor electronics module are "dummy displays", wherein they display the displayable sensor information received from the sensor electronics module without additional processing (e.g., prospective algorithmic processing necessary for real-time display of sensor information). In some embodiments, the displayable sensor information comprises transformed sensor data that does not require processing by the display device prior to display of the displayable sensor information. Some display devices may comprise software including display instructions (software programming comprising instructions configured to display the displayable sensor information and optionally query the sensor electronics module to obtain the displayable sensor information) configured to enable display of the displayable sensor information thereon. In some embodiments, the display device is programmed with the display instructions at the manufacturer and can include security and/or authentication to avoid plagiarism of the display device. In some embodiments, a display device is configured to display the displayable sensor information via a downloadable program (for example, a downloadable Java Script via the internet), such that any display device that supports downloading of a program (for example, any display device that supports Java applets) therefore can be configured to display displayable sensor information (e.g., mobile phones, tablets, PDAs, PCs and the like).

In some embodiments, certain display devices may be in direct wireless communication with the sensor electronics module, however intermediate network hardware, firmware, and/or software can be included within the direct wireless communication. In some embodiments, a repeater (e.g., a Bluetooth repeater) can be used to re-transmit the transmitted displayable sensor information to a location farther away than the immediate range of the telemetry module of the sensor electronics module, wherein the repeater enables direct wireless communication when substantive processing of the displayable sensor information does not occur. In some embodiments, a receiver (e.g., Bluetooth receiver) can be used to re-transmit the transmitted displayable sensor information, possibly in a different format, such as in a text message onto a TV screen, wherein the receiver enables direct wireless communication when substantive processing of the sensor information does not occur. In certain embodiments, the sensor electronics module directly wirelessly transmits displayable sensor information to one or a plurality of display devices, such that the displayable sensor information transmitted from the sensor electronics module is received by the display device without intermediate processing of the displayable sensor information.

In certain embodiments, one or more display devices comprise built-in authentication mechanisms, wherein authentication is required for communication between the sensor electronics module and the display device. In some embodiments, to authenticate the data communication between the sensor electronics module and display devices, a challenge-response protocol, such as a password authentication is provided, where the challenge is a request for the password and the valid response is the correct password, such that pairing of the sensor electronics module with the display devices can be accomplished by the user and/or manufacturer via the password.

In some embodiments, one or more display devices are configured to query the sensor electronics module for displayable sensor information, wherein the display device acts as a master device requesting sensor information from the sensor electronics module (e.g., a slave device) on-demand, for example, in response to a query. In some embodiments, the sensor electronics module is configured for periodic, systematic, regular, and/or periodic transmission of sensor information to one or more display devices (for example, every 1, 2, 5, or 10 minutes or more). In some embodiments, the sensor electronics module is configured to transmit data packages associated with a triggered alert (e.g., triggered by one or more alert conditions). However, any combination of the above described statuses of data transmission can be implemented with any combination of paired sensor electronics module and display device(s). For example, one or more display devices can be configured for querying the sensor electronics module database and for receiving alarm information triggered by one or more alarm conditions being met. Additionally, the sensor electronics module can be configured for periodic transmission of sensor information to one or more display devices (the same or different display devices as described in the previous example), whereby a system can include display devices that function differently with regard to how they obtain sensor information.

In some embodiments, as described in more detail elsewhere herein, a display device is configured to query the data storage memory in the sensor electronics module for certain types of data content, including direct queries into a database in the sensor electronics module's memory and/or requests for configured or configurable packages of data content therefrom; namely, the data stored in the sensor electronics module is configurable, queryable, predetermined, and/or pre-packaged, based on the display device with which the sensor electronics module is communicating. In some additional or alternative embodiments, the sensor electronics module generates the displayable sensor information based on its knowledge of which display device is to receive a particular transmission. Additionally, some display devices are capable of obtaining calibration information and wirelessly transmitting the calibration information to the sensor electronics module, such as through manual entry of the calibration information, automatic delivery of the calibration information, and/or an integral reference analyte monitor incorporated into the display device. U.S. Patent Publication No. US-2006-0222566-A1, U.S. Patent Publication No. US-2007-0203966-A1, U.S. Patent Publication No. US-2007-0208245-A1, and U.S. Patent Publication No. US-2005-0154271-A1, each of which are incorporated herein by reference in their entirety, describe systems and methods for providing an integral reference analyte monitor incorporated into a display device and/or other calibration methods that can be implemented with embodiments disclosed herein.

In general, a plurality of display devices (e.g., a custom analyte monitoring device, a mobile phone, a tablet, a smart watch, a reference analyte monitor, a drug delivery device, a medical device and a personal computer) are configured to wirelessly communicate with the sensor electronics module, wherein the one or more display devices are configured to display at least some of the displayable sensor information wirelessly communicated from the sensor electronics module, wherein displayable sensor information includes sensor data, such as raw data and/or transformed sensor data, such as analyte concentration values, rate of change information, trend information, alert information, sensor diagnostic information and/or calibration information, for example.

Exemplary Configurations

FIG. 1 is a diagram depicting an exemplary continuous analyte monitoring system 100 including an analyte sensor system 8 worn by a user 80 and a plurality of display devices 110, 120, 130, 140 according to certain aspects of the present disclosure. The analyte sensor system 8 includes a sensor electronics module 12 and a continuous analyte sensor 10 associated with the sensor electronics module 12. The sensor electronics module 12 is in direct wireless communication with one or more of the plurality of the display devices 110, 120, 130, and/or 140 shown.

In certain embodiments, the sensor electronics module 12 includes electronic circuitry associated with measuring and processing the continuous analyte sensor data, including prospective algorithms associated with processing and calibration of the sensor data. The sensor electronics module 12 can be physically connected to the continuous analyte sensor 10 and can be integral with (non-releasably attached to) or releasably attachable to the continuous analyte sensor 10. The sensor electronics module 12 may include hardware, firmware, and/or software that enables measurement of levels of the analyte via a glucose sensor. For example, the sensor electronics module 12 can include a potentiostat, a power source for providing power to the sensor, other components useful for signal processing and data storage, and a telemetry module for transmitting data from the sensor electronics module to one or more display devices. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, and/or a processor. The sensor electronics module 12 includes sensor electronics that are configured to process sensor information, such as sensor data, and generate transformed sensor data and displayable sensor information. Examples of systems and methods for processing sensor analyte data are described in more detail herein and in U.S. Pat. Nos. 7,310,544, 6,931,327, U.S. Patent Publication No. US-2005-0043598-A1, U.S. Patent Publication No. US-2007-0032706-A1, U.S. Patent Publication No. US-2007-0016381-A1, U.S. Patent Publication No. US-2008-0033254-A1, U.S. Patent Publication No. US-2005-0203360-A1, U.S. Patent Publication No. US-2005-0154271-A1, U.S. Patent Publication No. US-2005-0192557-A1, U.S. Patent Publication No. US-2006-0222566-A1, U.S. Patent Publication No. US-2007-0203966-A1, and U.S. Patent Publication No. US-2007-0208245-A1, each of which is incorporated herein by reference in its entirety for all purposes.

Referring again to FIG. 1, in some embodiments, the plurality of display devices (110, 120, 130, and/or 140) are configured for displaying (and/or alarming) the displayable sensor information that has been transmitted by the sensor electronics module 12 (e.g., in a customized data package that is transmitted to the display devices based on their respective preferences). In some embodiments, the plurality of display devices (110, 120, 130, and/or 140) are configured for receiving sensor data (e.g., analyte values) and displaying (and/or alarming) sensor information derived from the sensor data that has been transmitted by the sensor electronics module 12. Each of the display devices 110, 120, 130, or 140 can include a display such as a touchscreen display 112, 122, 132, /or 142 for displaying sensor information to a user and/or receiving inputs from the user. In some embodiments, the display devices may include other types of user interfaces such as voice user interface instead of or in addition to a touchscreen display for communicating sensor information to the user of the display device and/or receiving user inputs. In some embodiments, one, some or all of the display devices is configured to display or otherwise communicate the sensor information as it is communicated from the sensor electronics module (e.g., in a data package that is transmitted to respective display devices), without any additional prospective processing required for calibration and real-time display of the sensor data.

In the embodiment of FIG. 1, the plurality of display devices includes a custom application-specific display device 110 configured work with the analyte sensor system 8. In some embodiments, one of the plurality of display devices is a mobile phone 120 based on an Android or iOS operating system, a palm-top computer and/or the like, wherein the display device comprises a relatively larger display and is configured to display a graphical representation of the continuous sensor data (e.g., including current and historic data). Other display devices can include other hand-held devices, such as a tablet 130, a smart watch 140, an insulin delivery device, a blood glucose meter, and/or a desktop or laptop computer.

In this manner, a plurality of different display devices can be in direct wireless communication with the sensor electronics module (e.g., such as an on-skin sensor electronics module 12 that is physically connected to the continuous analyte sensor 10) during a sensor session to enable a plurality of different types and/or levels of display and/or functionality associated with the displayable sensor information, which is described in more detail elsewhere herein.

Continuous Sensor

In some embodiments, analyte sensor 10 of FIG. 1 comprises a continuous glucose sensor, for example a subcutaneous, transdermal (e.g., transcutaneous), or intravascular device. In some embodiments, the device can analyze a plurality of intermittent blood samples. The glucose sensor can use any method of glucose-measurement, including enzymatic, chemical, physical, electrochemical, spectrophotometric, polarimetric, calorimetric, iontophoretic, radiometric, immunochemical, and the like.

A glucose sensor can use any known method, including invasive, minimally invasive, and non-invasive sensing techniques (e.g., fluorescent monitoring), to provide a data stream indicative of the concentration of glucose in a host. The data stream is typically a raw data signal, which is converted into a calibrated and/or filtered data stream that is used to provide a useful value of glucose to a user, such as a patient or a caretaker (e.g., a parent, a relative, a guardian, a teacher, a doctor, a nurse, or any other individual that has an interest in the wellbeing of the host).

A glucose sensor can be any device capable of measuring the concentration of glucose. One exemplary embodiment is described below, which utilizes an implantable glucose sensor. However, it should be understood that the devices and methods described herein can be applied to any device capable of detecting a concentration of glucose and providing an output signal that represents the concentration of glucose.

In certain embodiments, the analyte sensor is an implantable glucose sensor, such as described with reference to U.S. Pat. No. 6,001,067 and U.S. Patent Publication No. US-2005-0027463-A1. In another embodiment, the analyte sensor is a transcutaneous glucose sensor, such as described with reference to U.S. Patent Publication No. US-2006-0020187-A1. In still other embodiments, the sensor is configured to be implanted in a host vessel or extracorporeally, such as is described in U.S. Patent Publication No. US-2007-0027385-A1, U.S. Patent Publication No. US-2008-0119703-A1, U.S. Patent Publication No. US-2008-0108942-A1, and U.S. Patent Application No. US-2007-0197890-A1. In one alternative embodiment, the continuous glucose sensor comprises a transcutaneous sensor such as described in U.S. Pat. No. 6,565,509 to Say et al., for example. In another alternative embodiment, the continuous glucose sensor comprises a subcutaneous sensor such as described with reference to U.S. Pat. No. 6,579,690 to Bonnecaze et al. or U.S. Pat. No. 6,484,046 to Say et al., for example. In another alternative embodiment, the continuous glucose sensor comprises a refillable subcutaneous sensor such as described with reference to U.S. Pat. No. 6,512,939 to Colvin et al., for example. In another alternative embodiment, the continuous glucose sensor comprises an intravascular sensor such as described with reference to U.S. Pat. No. 6,477,395 to Schulman et al., for example. In another alternative embodiment, the continuous glucose sensor comprises an intravascular sensor such as described with reference to U.S. Pat. No. 6,424,847 to Mastrototaro et al., for example.

Figure 2A:
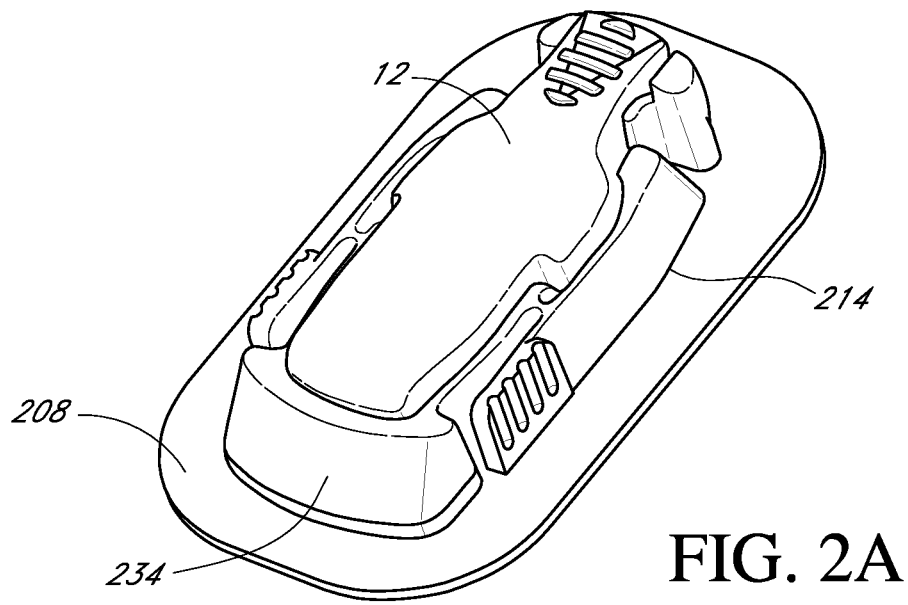
FIG. 2A is a perspective view of an exemplary sensor system that can embody the analyte sensor system according to certain aspects of the present disclosure.
Figure 2B:
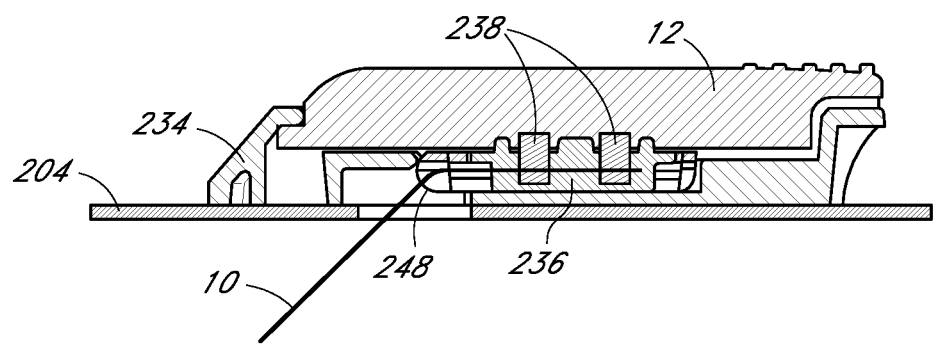
FIG. 2B is a side view of an exemplary sensor system that can embody the analyte sensor system according to certain aspects of the present disclosure.

FIGS. 2A and 2B are perspective and side views of an exemplary sensor system that can incorporate the analyte sensor system 8 shown in FIG. 1 according certain aspects of the present disclosure. The sensor system includes a mounting unit 214 and sensor electronics module 12 attached thereto in certain embodiments, shown in its functional position, including a mounting unit and a sensor electronics module matingly engaged therein. In some embodiments, the mounting unit 214, also referred to as a housing or sensor pod, comprises a base 234 adapted for fastening to a host's skin. The base can be formed from a variety of hard or soft materials, and can comprises a low profile for minimizing protrusion of the device from the host during use. In some embodiments, the base 234 is formed at least partially from a flexible material, which is believed to provide numerous advantages over conventional transcutaneous sensors, which, unfortunately, can suffer from motion-related artifacts associated with the host's movement when the host is using the device. The mounting unit 214 and/or sensor electronics module 12 can be located over the sensor insertion site to protect the site and/or provide a minimal footprint (utilization of surface area of the host's skin).

In some embodiments, a detachable connection between the mounting unit 214 and sensor electronics module 12 is provided, which enables improved manufacturability, namely, the relatively inexpensive mounting unit 214 can be disposed of when replacing the sensor system after its usable life, while the relatively more expensive sensor electronics module 12 can be reusable with multiple sensor systems. In some embodiments, the sensor electronics module 12 is configured with signal processing (programming), for example, configured to filter, calibrate and/or other algorithms useful for calibration and/or display of sensor information. However, an integral (non-detachable) sensor electronics module can be configured.

In some embodiments, the contacts 238 are mounted on or in a subassembly hereinafter referred to as a contact subassembly 236 configured to fit within the base 234 of the mounting unit 214 and a hinge 248 that allows the contact subassembly 236 to pivot between a first position (for insertion) and a second position (for use) relative to the mounting unit 214. The term "hinge" as used herein is a broad term and is used in its ordinary sense, including, without limitation, to refer to any of a variety of pivoting, articulating, and/or hinging mechanisms, such as an adhesive hinge, a sliding joint, and the like; the term hinge does not necessarily imply a fulcrum or fixed point about which the articulation occurs. In some embodiments, the contacts 238 are formed from a conductive elastomeric material, such as a carbon black elastomer, through which the sensor 10 extends.

In certain embodiments, the mounting unit 214 is provided with an adhesive pad 208, disposed on the mounting unit's back surface and includes a releasable backing layer. Thus, removing the backing layer and pressing the base portion 234 of the mounting unit onto the host's skin adheres the mounting unit 214 to the host's skin. Additionally or alternatively, an adhesive pad can be placed over some or all of the sensor system after sensor insertion is complete to ensure adhesion, and optionally to ensure an airtight seal or watertight seal around the wound exit-site (or sensor insertion site) (not shown). Appropriate adhesive pads can be chosen and designed to stretch, elongate, conform to, and/or aerate the region (e.g., host's skin). The embodiments described with reference to FIGS. 2A and 2B are described in more detail with reference to U.S. Pat. No. 7,310,544, which is incorporated herein by reference in its entirety. Configurations and arrangements can provide water resistant, waterproof, and/or hermetically sealed properties associated with the mounting unit/sensor electronics module embodiments described herein.

Various methods and devices that are suitable for use in conjunction with aspects of some embodiments are disclosed in U.S. Patent Publication No. US-2009-0240120-A1, which is incorporated herein by reference in its entirety for all purposes.

Figure 3:
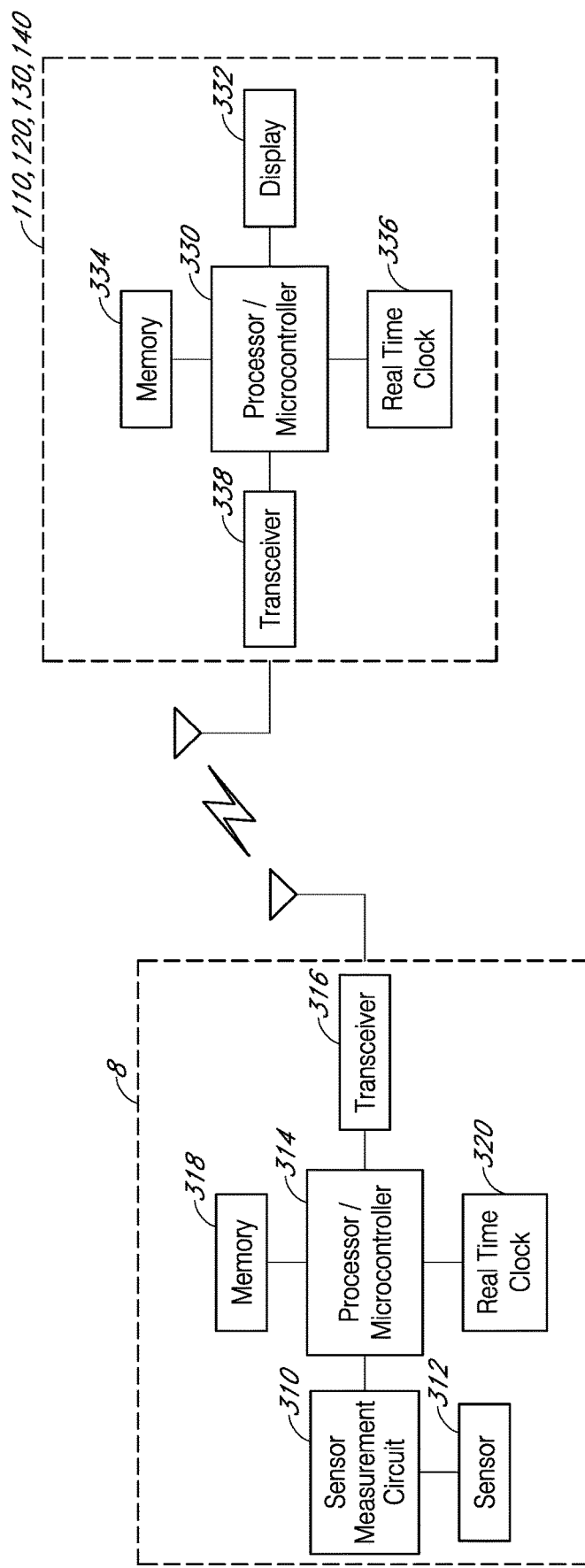
FIG. 3 is an exemplary block diagram illustrating various elements of certain embodiments of a continuous analyte monitoring system comprising an analyte sensor system and a plurality of display devices according to certain aspects of the present disclosure.

FIG. 3 is an exemplary block diagram illustrating various elements of certain embodiments of a continuous analyte monitoring system 300 comprising analyte sensor system 8 and display devices 110, 120, 130, 140. The analyte sensor system 8 may include an analyte sensor 312 (also designated 10 in FIG. 1) coupled to a sensor measurement circuit 310 for processing and managing sensor data. The sensor measurement circuit 310 may be coupled to a processor 314 (part of item 12 in FIG. 1). In some embodiments, the processor 314 may perform part or all of the functions of the sensor measurement circuit 310 for obtaining and processing sensor measurement values from the sensor 312. The processor may be further coupled to a radio unit or transceiver 316 (part of item 12 in FIG. 1) for sending sensor data and receiving requests and commands from an external device, such as the display device 110, 120, 130, 140, which is used to display or otherwise provide the sensor data to a user. As used herein, the terms "radio unit" and "transceiver" are used interchangeably and generally refer to a device that can wirelessly transmit and receive data. The analyte sensor system 8 may further include a memory 318 (part of item 12 in FIG. 1) and a real time clock (RTC) 320 (part of item 12 in FIG. 1) for storing and tracking sensor data.

Wireless communication protocols may be used to transmit and receive data between the sensor system 8 and the display device 110, 120, 130, 140. The wireless protocol used may be designed for use in a wireless sensor network that is optimized for periodic and small data transmissions (that may be transmitted at low rates if necessary) to and from multiple devices in a close range (e.g., a personal area network (PAN)). For example, the protocol may be optimized for periodic data transfers where transceivers may be configured to transmit data for short intervals and then enter low power modes for long intervals. The protocol may have low overhead requirements both for normal data transmissions and for initially setting up communication channels (e.g., by reducing header overhead) to reduce power consumption. In some embodiments, burst broadcasting schemes (e.g., one way communication) may be used. This may eliminate overhead required for acknowledgement signals and allow for periodic transmissions that consume little power.

The protocol may further be configured to establish communication channels with multiple devices while implementing interference avoidance schemes. In some embodiments, the protocol may make use of adaptive isochronous network topologies that define various time slots and frequency bands for communication with several devices. The protocol may thus modify transmission windows and frequencies in response to interference and to support communication with multiple devices. Accordingly, the wireless protocol may use time and frequency division multiplexing (TDMA) based schemes. The wireless protocol may also employ direct sequence spread spectrum (DSSS) and frequency-hopping spread spectrum schemes. Various network topologies may be used to support short-distance and/or low-power wireless communication such as peer-to-peer, start, tree, or mesh network topologies such as WiFi, Bluetooth and Bluetooth Low Energy (BLE). The wireless protocol may operate in various frequency bands such as an open ISM band such as 2.4 GHz. Furthermore, to reduce power usage, the wireless protocol may adaptively configure data rates according to power consumption.

The display device 110, 120, 130, 140 may be used for alerting and providing sensor information to a user, and may include a processor 330 for processing and managing sensor data. The display device 110, 120, 130, 140 may include a display 332, a memory 334, and a real time clock 336 for displaying, storing and tracking sensor data respectively. The display device 110, 120, 130, 140 may further include a radio unit or transceiver 338 for receiving sensor data and for sending requests, instructions, and data to the analyte sensor system 8. The transceiver 338 may further employ a communication protocol. The memory 334 may also be used for storing an operating system for the display device and/or a custom (e.g., proprietary) application designed for wireless data communication between a transceiver and the display device. The memory 334 may be a single memory device or multiple memory devices and may be a volatile or non-volatile memory for storing data and/or instructions for software programs and applications. The instructions may be executed by the processor 330 to control and manage the transceiver 338.

In some embodiments, when a standardized communication protocol is used, commercially available transceiver circuits may be utilized that incorporate processing circuitry to handle low level data communication functions such as the management of data encoding, transmission frequencies, handshake protocols, and the like. In these embodiments, the processor 314, 330 does not need to manage these activities, but rather provides desired data values for transmission, and manages high level functions such as power up or down, set a rate at which messages are transmitted, and the like. Instructions and data values for performing these high level functions can be provided to the transceiver circuits via a data bus and transfer protocol established by the manufacturer of the transceiver circuit 316.

Components of the analyte sensor system 8 may require replacement periodically. For example, the analyte sensor system 8 may include an implantable sensor 312 that may be attached to a sensor electronics module that includes the sensor measurement circuit 310, the processor 314, memory 318, and transceiver 316, and battery (not shown). The sensor 312 may require periodic replacement (e.g., every 7-30 days). The sensor electronics module may be configured to be powered and active for much longer than the sensor 312 (e.g., for three, six months or more) until the battery needs replacement. Replacing these components may be difficult and require the assistance of trained personnel. Reducing the need to replace such components, particularly the battery, significantly improves the convenience of the analyte sensor system 8 to the user. In some embodiments, the sensor session as defined above may correspond to the life of the sensor 312 (e.g., in the range of 7 to 30 days). When a sensor electronic module is used for the first time (or reactivated once a battery has been replaced in some cases), it may be connected to a sensor 312 and a sensor session may be established. As will be further described below, there may be a process for initially establishing communication between a display device 110, 120, 130, 140 and the sensor electronics module when it is first used or re-activated (e.g., the battery is replaced). Once the display device 110, 120, 130, 140 and sensor electronics module have established communication, the display device 110, 120, 130, 140 and sensor electronics module may periodically and/or continuously be in communication over the life of several sensors 312 until, for example, the battery needs to be replaced. Each time a sensor 312 is replaced, a new sensor session may be established. The new sensor session may be initiated through a process completed using a display device 110, 120, 130, 140 and the process may be triggered by notifications of a new sensor via the communication between the sensor electronics module and the display device 110, 120, 130, 140 that may be persistent across sensor sessions.

The analyte sensor system 8 gathers analyte data from the sensor 312 that it periodically sends to the display device 110, 120, 130, 140. Data points are gathered and transmitted over the life of the sensor (e.g., in the range of 1 to 30 days or more). New measurements may need to be transmitted often enough to adequately monitor glucose levels. Rather than having the transmission and receiving circuitry of each of the sensor system 8 and display device 110, 120, 130, 140 continuously communicating, the analyte sensor system 8 and display device 110, 120, 130, 140 may regularly and periodically establish a communication channel between them. Thus, sensor system 8 can communicate via wireless transmission with display device 110, 120, 130, 140 (e.g., a hand-held computing device) at predetermined time intervals. The duration of the predetermined time interval can be selected to be long enough so that the sensor system 8 does not consume too much power by transmitting data more frequently than needed, yet frequent enough to provide substantially real-time sensor information (e.g., measured glucose values) to the display device 110, 120, 130, 140 for output (e.g., display) to a user. While the predetermined time interval is every five minutes in some embodiments, it is appreciated that this time interval can be varied to be any desired length of time.

Figure 4:
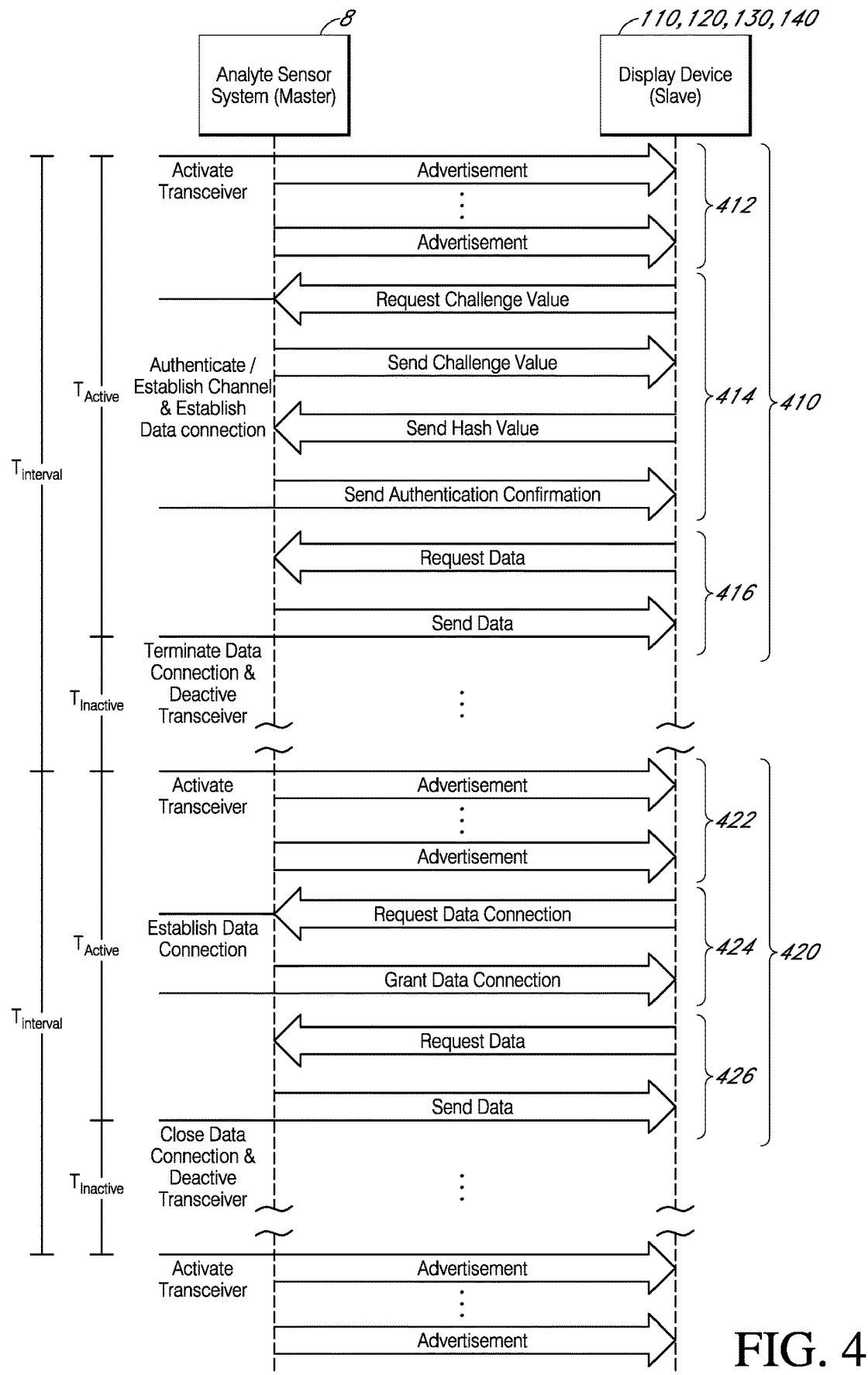
FIG. 4 is a flow diagram illustrating an exemplary wireless data communication procedure between an analyte sensor system and a display device capable of wireless receiving analyte values from the analyte sensor system according to certain aspects of the present disclosure.

FIG. 4 is a flow diagram illustrating an exemplary wireless data communication procedure between an analyte sensor system 8 and a display device 110, 120, 130, 140 capable of wirelessly receiving analyte values from the analyte sensor system 8 according to certain aspects of the present disclosure. The various tasks performed in connection with the procedure illustrated in FIG. 4 may be performed by a processor executing instructions embodied in non-transitory computer-readable medium. For example, the tasks performed in connection with the procedure may be performed by hardware, software, firmware, or any combination thereof incorporated into one or more of computing devices, such as one or more of sensor system 8 and display devices 110, 120, 130 and 140 of FIG. 1 and/or FIG. 3. It should be appreciated that the procedure may include any number of additional or alternative tasks. The tasks shown in FIG. 4 need not be performed in the illustrated order, and the procedure may be incorporated into a more comprehensive procedure or process having additional functionality not described in detail herein.

In the example described below, the analyte values are glucose values based on one or more measurements of glucose level by the analyte sensor 312 for illustration purposes. However, it should be understood that the analyte values can be any other analyte value described herein. The wireless data communication between the analyte sensor system 8 and the display device may happen periodically, at times separated by an update interval denoted "$T_{interval}$" that may correspond to a time duration between two consecutive wireless communication sessions between the transceiver 316 of the analyte sensor system 8 and the transceiver 338 of the display device 110, 120, 130, 140. Alternatively, the update interval may be thought of as a period of obtaining and sending a recently measured glucose value. Transmitting advertisement signals, establishing a data connection (e.g., a communication channel) and requesting and sending data may occur during wireless communication sessions each lasting an active time or period denoted "$T_{Active}$" within an update interval $T_{interval}$. In between two consecutive wireless communication sessions, the transceiver 316 goes into an inactive or sleep mode for an inactive period denoted as "$T_{Inactive}$" to conserve battery life and/or reduce peak voltage requirements, for example.

FIG. 4 shows two such wireless communication sessions, namely, a first wireless communication session 410 and a second wireless communication session 420. Each wireless communication session 410, 420 starts with the analyte sensor system 8 establishing a data connection with a display device 110, 120, 130, 140. To establish a data connection with the display device 110, 120, 130, 140, the transceiver 316 of the analyte sensor system 8 transmits a series of advertisement signals 412 during the first wireless communication session 420. Each advertisement signal may be considered an invitation for a display device 110, 120, 130, 140 to establish a data connection with the transceiver 316.

In the illustrated example of FIG. 4, it is assumed that the analyte sensor system 8 needs to engage in an initial system setup because the system 8 has been just turned on for the first time and/or is currently not paired with a display device 110, 120, 130, 140. Typically, a user of the display device 110, 120, 130, 140 identifies a new or never-been used analyte sensor system 8 that needs to be paired with the display device by entering identification information (e.g., a serial number) associated with the new/unpaired analyte sensor system 8 via a custom application running on the display device using a user interface (e.g., a touchscreen display). During the first wireless communication session 410, an authentication procedure needs to be performed as part of a data connection process 414. To establish a data connection with the analyte sensor system 8, the display device 110, 120, 130, 140 listens continuously until an advertisement signal transmitted by the transceiver 316 of the analyte sensor system 8 is received. Once the transceiver 316 begins transmitting advertisement signals 412, it may take one, two, or more advertisement signals for the display device 110, 120, 130, 140 to receive the advertisement signal and responds to the advertisement signal. In some embodiments, the transceiver 316 stops sending additional advertisement signals once a display device receives an advertisement signal and responds to the advertisement signal, for example, via an acknowledgement. In other embodiments, the transceiver 316 may continue to send additional advertisement signals even after receiving a response from a display device so that another display device may receive and respond to one of the additional advertisement signals.

After an advertisement signal is successfully received by a display device 110, 120, 130, 140, the display device and the analyte sensor system 8 engage in a first data connection process 414. During the first data connection process 414, the display device requests a challenge value from the analyte sensor system 8 and the analyte sensor system 8 sends the change value to the display device in response. Upon receiving the challenge value, the display device calculates a hash value based on the challenge value and the identification information associated with the analyte sensor system 8 and/or the transceiver 316 and sends the hash value to the transceiver 316. The transceiver 316 receives the hash value from the display device 110, 120, 130, 140, decodes the identification information from the hash value, and verifies that the received identification information matches identification information associated with the sensor system 8 and/or transceiver 316 previously stored in the memory 318 of the analyte sensor system 8, such as during manufacturing of the sensor system 8. Upon verification, the transceiver 316 sends a signal confirming a successful authentication to the display device 110, 120, 130, 140. Once authenticated, the analyte sensor system 8 and display device 110, 120, 130, 140 may exchange information to determine how data will be exchanged (e.g., a specific frequency, time slot assignment, encryption, etc.).

After completion of the first data connection process 414, the analyte sensor system 8 and the connected display device 110, 120, 130, 140 engage in a first data communication 416 during which the connected display device requests and receives desired information (e.g., analyte data, control information, identification information, and/or instruction) from the analyte sensor system 8. When the first data communication 416 is completed, the data connection is terminated (e.g., by closing the established communication channel) and the transceiver 316 and/or the processor 314 of the analyte sensor system 8 (and possibly the transceiver 338 and/or the processor 330 of the display device 110, 120, 130, 140 as well, depending on implementation preference) can be deactivated by causing the transceiver 316 and/or the processor 314 to enter a sleep or inactive mode. In some embodiments, the transceiver 316 is completely powered down during a sleep mode. In other embodiments, the transceiver 316 is in a low power mode using only a small fraction (e.g., 1-10%) of the normal current/power.

The active period $T_{Active}$ corresponding to a duration of each wireless communication session may be a small fraction of the update interval $T_{interval}$ corresponding to a period between two consecutive wireless communication sessions. For example, $T_{interval}$ may be between about 200 and 400 seconds and $T_{Active}$ may be between 20 and 40 seconds. As such, the transceiver 316 of the analyte sensor system 8 may be powered fully for only 10 percent (e.g., 30 seconds) of a five minute $T_{interval}$. This may significantly reduce power consumption and peak voltage demand. In some cases, the transceiver 316 is not completely powered down, but enters a low-power mode when not transmitting. After an inactive time or period $T_{Inactive}$, a second wireless communication session 420 starts when the transceiver 316 (and the transceiver 338) powers up again, begins transmitting a second series of advertisement signals 422, engages in a second data connection process 424 and a second data communication process 426 with the transceiver 338 of the display device 110, 120, 130, 140 as shown in FIG. 4. Unlike the first data connection process 414, however, the second data connection process 424 does not involve an authentication because the analyte sensor system 8 and the display device 110, 120, 130, 140 have been successfully paired or bonded during the first wireless communication session 410 as described above. This process may continue, with new data connections and communications being completed at the predetermined intervals. During all or part of each inactive period $T_{Inactive}$ during which the transceiver 316 is in a sleep mode, the processor 314 can take measurement(s) of one or more analyte values using the analyte sensor 312 and the sensor measurement circuitry 310. For example, the processor 314 may take multiple analyte value measurements and average them to generate a single averaged analyte value to be transmitted in a next wireless communication session.

Continuously re-establishing a new communication channel to allow for partially or wholly powering down the transceiver 316 during each update interval $T_{interval}$ can provide significant power savings and can allow the sensor electronics module 12 (FIG. 1) to operate continuously for six months or more without requiring a battery replacement. Furthermore, rather than blindly transmitting glucose data points during the update interval $T_{interval}$, establishing specific data connections (e.g., communication channels) with only the desired display devices 110, 120, 130, 140 can prevent unauthorized use and interception of glucose measurement values. In some embodiments, only a subset of multiple display devices 110, 120, 130, 140 can be configured to receive different data such as glucose measurement values and/or alarm conditions. This has a benefit of preventing multiple display devices from issuing alarms, thereby confusing and/or frustrating the user. In addition, by establishing a secure two-way communication channel, requests for specific glucose measurement values or communication of calibration or configuration information may be transmitted on an as-needed/requested basis between the analyte sensor system 8 and display device 110, 120, 130, 140.

Also, in some embodiments, the transceiver 316 may not be activated for data communication every update interval $T_{interval}$. Instead, the transceiver 316 may be activated every second, third or fourth update interval $T_{interval}$, for example, so that communication between the sensor system 8 with the display device 110, 120, 130, 140 occurs less frequently than every update interval $T_{interval}$. Doing so can further reduce power consumption. Activation could also depend on the sensor data. For example, only activate the transceiver if data meets certain thresholds, such a current rate of change, current high value, current low value, absolute difference from a previously exchanged value, percentage difference from a previously exchanged value, and the like. In some embodiments, instead of skipping certain fixed update intervals, the length of each interval can be made vary based on sensor data. For example, if the sensor data indicates a low glucose value and/or a hypoglycemic reaction is detected, the update interval value can be shortened from a normal update interval value so that more frequent readings are taken and transmitted.

In some embodiments, the update interval $T_{interval}$, the active period $T_{Active}$ and a frequency $F_{Activation}$ by which the transceiver is activated (e.g., every second, third or fourth update interval) may be variable. In certain embodiments, the above-identified parameters can be user configurable (e.g., by inputting a value for the variable using user interface of display device 110, 120, 130, 140) and/or automatically varied by the analyte sensor system 8 or display device 110, 120, 130, 140 based on one or more criteria. The criteria can include: (i) a monitored battery power of the sensor system 8, (ii) a currently measured, previously measured and/or predicted glucose concentrations meeting or exceeding a predetermined threshold, (iii) a glucose concentration trend of the host based on currently measured, previously measured and/or predicted glucose concentrations, (iv) a rate of change of glucose concentration of the host based currently measured, previously measured and/or predicted glucose concentrations meeting or exceeding a predetermined threshold, (v) whether the host is determined to be in or near hyperglycemia based on currently measured, previously measured and/or predicted glucose concentrations, (vi) whether the host is determined to be in or near hypoglycemia based on currently measured, previously measured and/or predicted glucose concentrations, (vii) user inputted activity of the host (e.g., exercising or sleeping), (viii) time since a sensor session has started (e.g., when a new sensor 10 is used), (ix) one or more errors detected by sensor system 8 or display device 110, 120, 130, 140, and (x) type of display device.

$T_{interval}$, $T_{Active}$, $F_{Activation}$ and/or other configuration items described herein may form part of a communication protocol profile that may be stored on any device that implements the fundamental communication protocol to allow for a customized use of the protocol for communicating analyte measurement values in the analyte sensor system 10 and display device 110, 120, 130, 140.

Monitoring and Managing Battery Life

The analyte sensor system 8 worn by the user 80 is powered by a battery (not shown in FIGS. 1 and 3). As the battery's power level gets depleted, the analyte sensor system 8 may not be able to perform one or more functions and will eventually stop functioning altogether. For example, as the battery power level falls below a certain threshold amount, the analyte sensor system 8 may not be able to transmit analyte values using the transceiver 316 because the output voltage of the battery would be pulled below a threshold operation voltage of the transceiver 316 at a load current required for the transmission. At some intermediate level, it may be possible for the transceiver 316 to perform regularly-scheduled transmissions of analyte values but not bulk-transfers of stored past analyte values. This is because the bulk transfer operation typically makes use of a special transmission mode of the transceiver that draws a higher amount of current and/or requires a higher voltage as compared to a transmission mode used for regularly-scheduled transmissions. It is therefore desirable to monitor the current power level of the battery installed in the analyte sensor system 8 to allow for continued use. By knowing the current battery power level, for example, it is possible to predict remaining useful life of the battery based the current power level and assumed future usage of the analyte sensor system 8. The analyte sensor system 8 may transmit data indicating the current power level and/or the predicted remaining useful life to the display device 110, 120, 130, 140 so that such information can be displayed to the user. In addition, it is possible to disable one or more functions of the analyte sensor system 8 when the current power level falls below a predetermined threshold power level and/or the predicted remaining useful life becomes less than a predetermined threshold time. In addition, the analyte sensor system 8 may transmit alerts to the display device 110, 120, 130, 140 indicating such low battery conditions exist.

Figure 5:
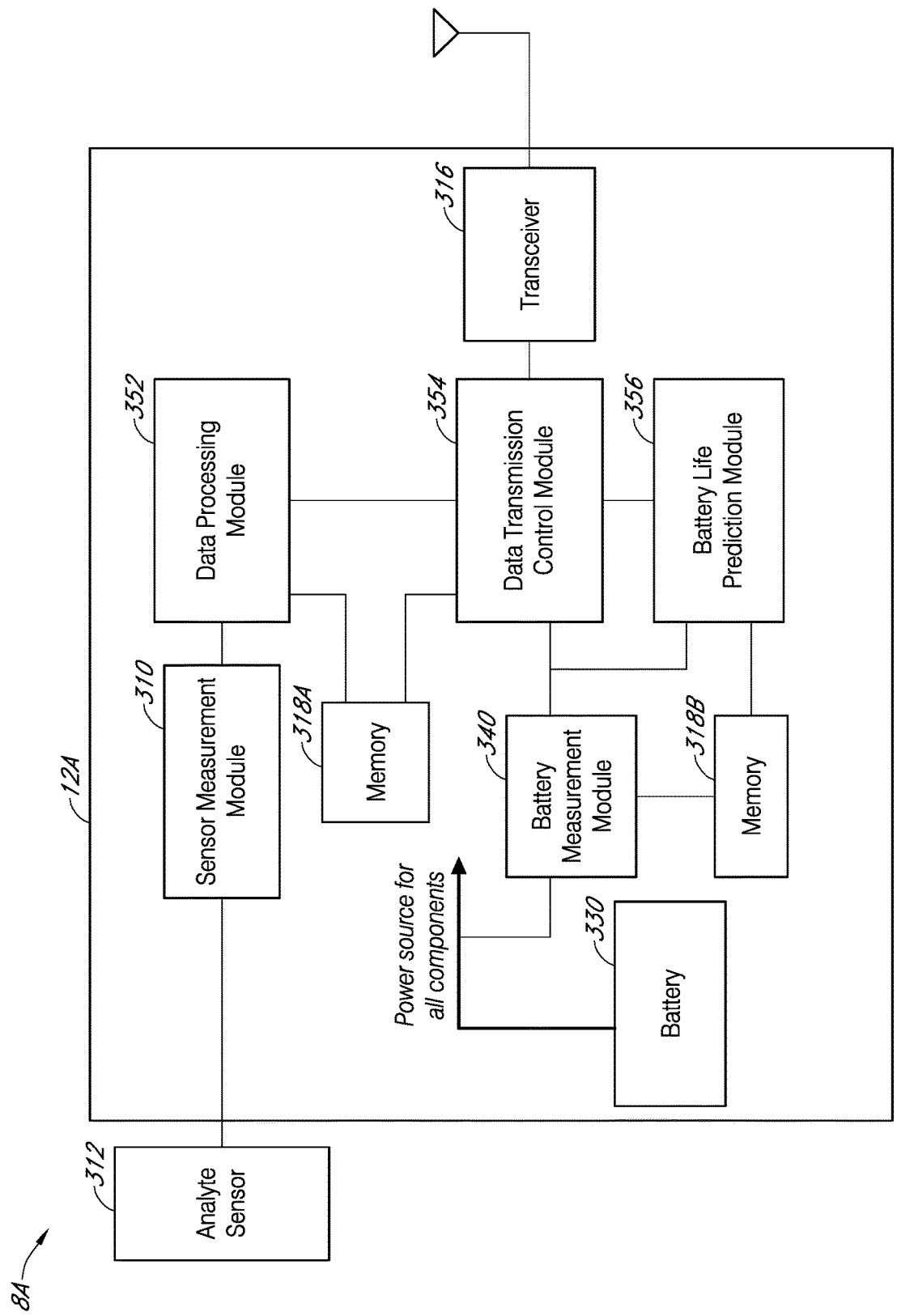
FIG. 5 is an exemplary block diagram of certain embodiments of an analyte sensor system capable of monitoring a current power level of a battery installed in the analyte sensor system and predicting remaining useful life of the battery according to certain aspects of the present disclosure.

FIG. 5 is an exemplary block diagram of certain embodiments of an analyte sensor system 8A capable of monitoring a current power level of a battery 330 installed in the analyte sensor system 8A and predicting remaining useful life of the battery 330 according to certain aspects of the present disclosure. The analyte sensor system 8A includes an analyte sensor 312 and a sensor electronics module 12A. In certain embodiments, the analyte sensor 312 is a continuous glucose sensor implantable in a user and capable of providing an output signal that represents the user's blood glucose level. The sensor electronics module 12A includes a sensor measurement module 310 coupled to the analyte sensor 312 and configured for measuring the output signal from the analyte sensor 312 and providing analyte values (e.g., glucose values), and a data processing module 352 coupled to the sensor measurement module 310 and configured for processing the analyte values such as averaging the analyte values and/or storing the analyte values in a memory 318A.

The sensor electronics module 12A also includes a data transmission control module 354 coupled to the data processing module 352 and configured for causing a transceiver 316 to transmit wireless signals including the analyte values to a display device 110, 120, 130, 140 (FIGS. 1 and 3) configured to display the analyte values. The data transmission control module 354 can be also configured for causing the transceiver 316 to perform a bulk transfer of past analyte values stored in the memory 310 using a special transmission mode of the transceiver. For example, if the display device 110, 120, 130, 140 is powered off or otherwise not available for communication with the analyte sensor system 8A, the analyte sensor system 8A may measure and store the analyte values in the memory 318A. When the display device 110, 120, 130, 140 is later powered on or otherwise becomes available, the analyte sensor system 8 may perform a bulk transfer of the stored past analyte values upon a request by the display device 110, 120, 130, 140.

The sensor electronics module 12A also includes a battery 330 configured for providing electrical power to all power-consuming components of the analyte sensor system 8A, and a battery measurement module 340 coupled to the battery 330 and configured for measuring a value indicative of a current power level of the battery 330 and providing the measured value to the data transmission control module 354 and a battery life prediction module 356 described below. The battery life prediction module 356 is coupled to the battery measurement module 340 and the data transmission control module 354 and configured for predicting remaining useful life of the battery based on the measured value indicative a current power level of the battery 330 and assumed future usage of the analyte sensor system 8A. The assumed future usage can be determined based on history of past usages (e.g., average and peak current levels and frequencies of regularly-scheduled transmissions and bulk transfers) stored in the memory 318A or a memory 318B. In certain embodiments, the data transmission control module 354 is configured for controlling one or more data transmission functions of the analyte sensor system 8A based on the measured value indicative of the current power level of the battery 330 and/or the predicted remaining useful life of the battery 330.

Figure 6A:
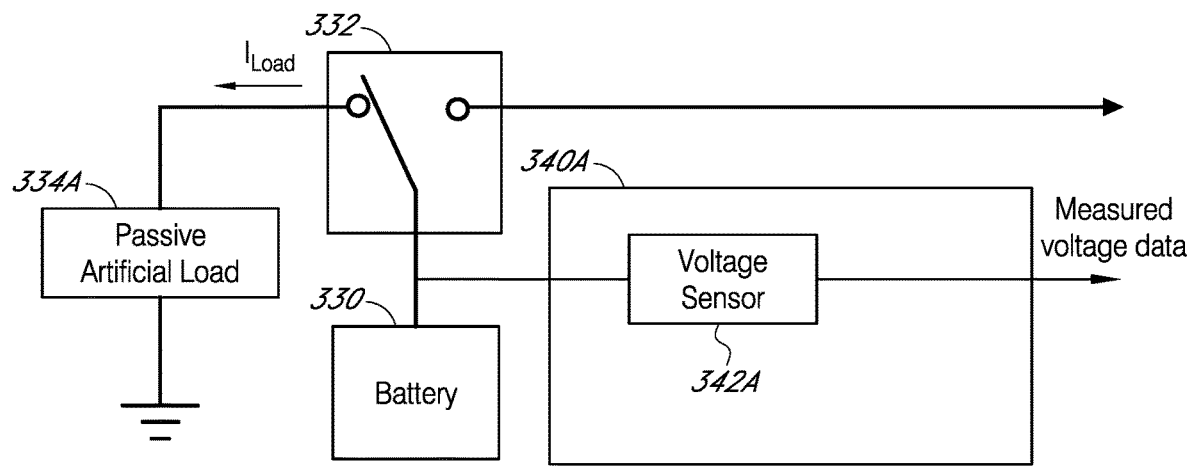
FIG. 6A is a diagram depicting a first exemplary arrangement comprising a battery measurement module configured to measure a voltage drop indicative of an internal resistance of the battery according to certain aspects of the present disclosure.
Figure 6B:
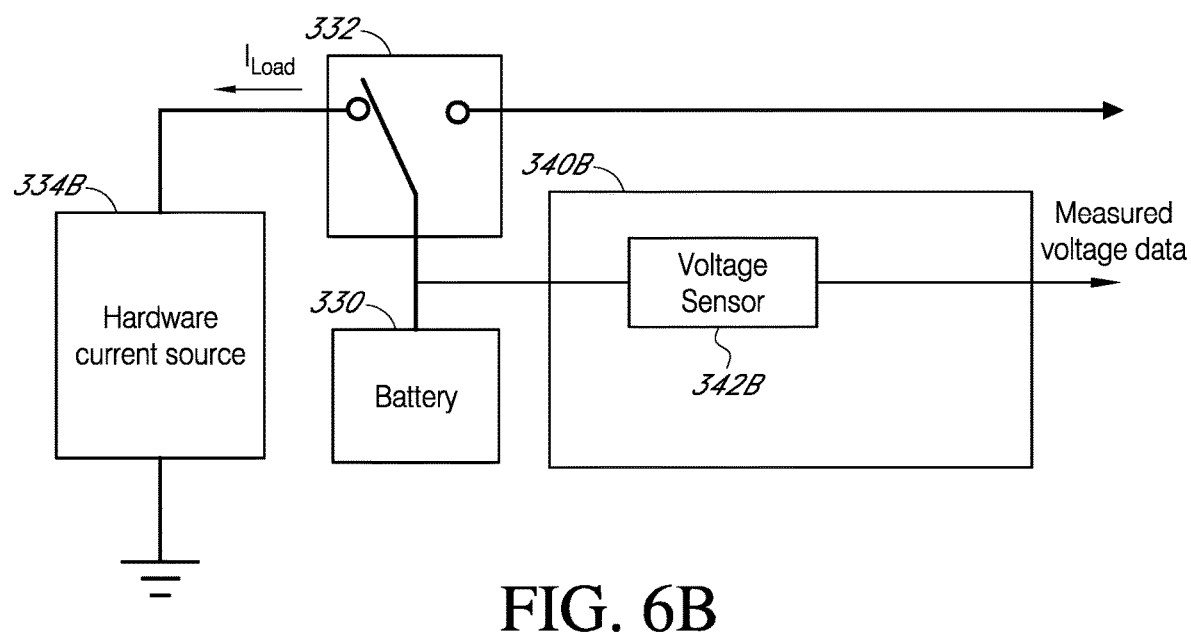
FIG. 6B is a diagram depicting a second exemplary arrangement comprising a battery measurement module configured to measure a voltage drop indicative of an internal resistance of the battery according to certain aspects of the present disclosure.
Figure 6C:
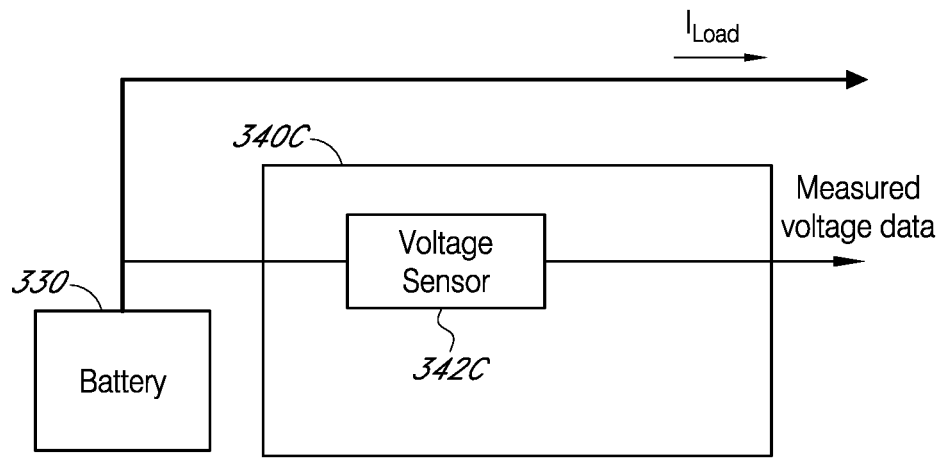
FIG. 6C is a diagram depicting a third exemplary arrangement comprising a battery measurement module configured to measure a voltage drop indicative of an internal resistance of the battery according to certain aspects of the present disclosure.

There are many different ways of implementing the battery measurement module 340 to measure the current power level of the battery 330. With some batteries, the internal resistance increases as the battery's power level drops. Thus, the internal resistance can be a good indicator of the current power level of the battery. FIGS. 6A, 6B and 6C are diagrams depicting three different exemplary arrangements comprising battery measurement modules 340A, 340B, 340C configured to measure a voltage drop indicative of an internal resistance of the battery 330 according to certain aspects of the present disclosure. In all three arrangements depicted in FIGS. 6A, 6B and 6C, the battery measurement modules 340A, 340B, 340C include a voltage sensor 342A, 342B, 342C (e.g., an A/D converter) configured to measure a voltage drop at the battery 330.

In order to determine the internal resistance and current power level of the battery, it is necessary to measure the voltage drop while the battery 330 is connected to a load that draws a known current. In arrangements of FIGS. 6A and 6B, the battery 330 is disconnected from the actual load (i.e., the components of the sensor electronics module 12A) by the use of a switch 332 and is instead connected to artificial loads 334A, 336B with known impedance or current-drawing characteristics. In the arrangement of FIG. 6A, for example, the artificial load is a passive artificial load comprising passive electrical components such as a capacitor and/or a resistor. Because the impedance of the passive artificial load is known, it is possible to determine the internal resistance of the battery by monitoring the current flowing into the load as a function of time. In the arrangement of FIG. 6B, the artificial load is an active artificial load or hardware comprising active components such as an operational amplifier or a MOSFET configured as a constant current source. The use of an active load configured to draw a constant current from the battery 330 can considerably simplify the determination of the internal resistance of the battery.

In the arrangement shown in FIG. 6C, the voltage sensor 342C in the battery measurement module 340C measures a voltage drop while the analyte sensor system 8A performs one or more tasks known to draw a constant current from the battery 330. Such tasks can include a specific wireless transmission mode. For example, in analyte sensor systems employing an ANT radio protocol, a transmission mode known as "ANT-FS" mode is known to draw a constant current from the battery. The ANT-FS mode is used for a bulk transfer of data items stored in a database and, in analyte sensor systems employing the ANT radio protocol, the ANF-FS mode is typically used for a bulk transfer of stored past analyte values. In the arrangement of FIG. 6C, the battery measurement module 340 can be configured to measure the voltage drop at the battery 330 while the transceiver 316 is engaged in a specific wireless transmission mode (e.g., the ANT-FS mode) known to draw a constant current from the battery 330. In some embodiments, the voltage drop measurement can be made while the transceiver 316 is engaged a "fake" ANT-FS mode whereby the transceiver transmits "dummy" data such as all 0's or all 1's.

After determining the voltage drop, the current power level of the battery 330 can be determined using one of a variety of methods known in the art. In some embodiments, a predetermined voltage profile curve associated with the battery 330 is stored in a memory (e.g., the memory 318B) and the current power level is determined by comparing the measured voltage drop to the stored voltage profile curve.

Figure 6D:
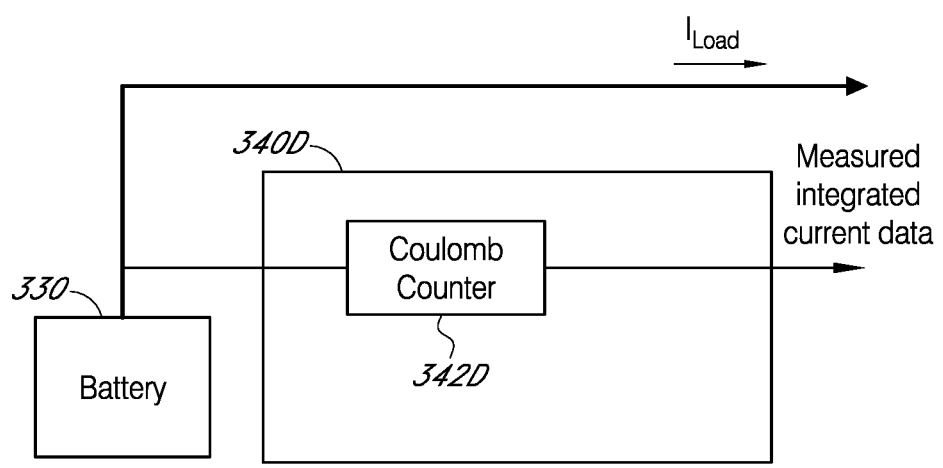
FIG. 6D is a diagram depicting an exemplary arrangement in which the battery measurement module includes a Coulomb counter according to certain aspects of the present disclosure.

FIG. 6D is a diagram depicting an exemplary arrangement in which the battery measurement module 340D includes a Coulomb counter 342D according to certain aspects of the present disclosure. The Coulomb counter 342D is a device configured to provide a value indicative of an accumulated amount of charges drawn from the battery or an integral of a load current drawn from the battery over time. By knowing the accumulated amount of charges drawn from the battery 330, it is possibly to determine the current power level (e.g., state of charge) of the battery 330.

Figure 7:
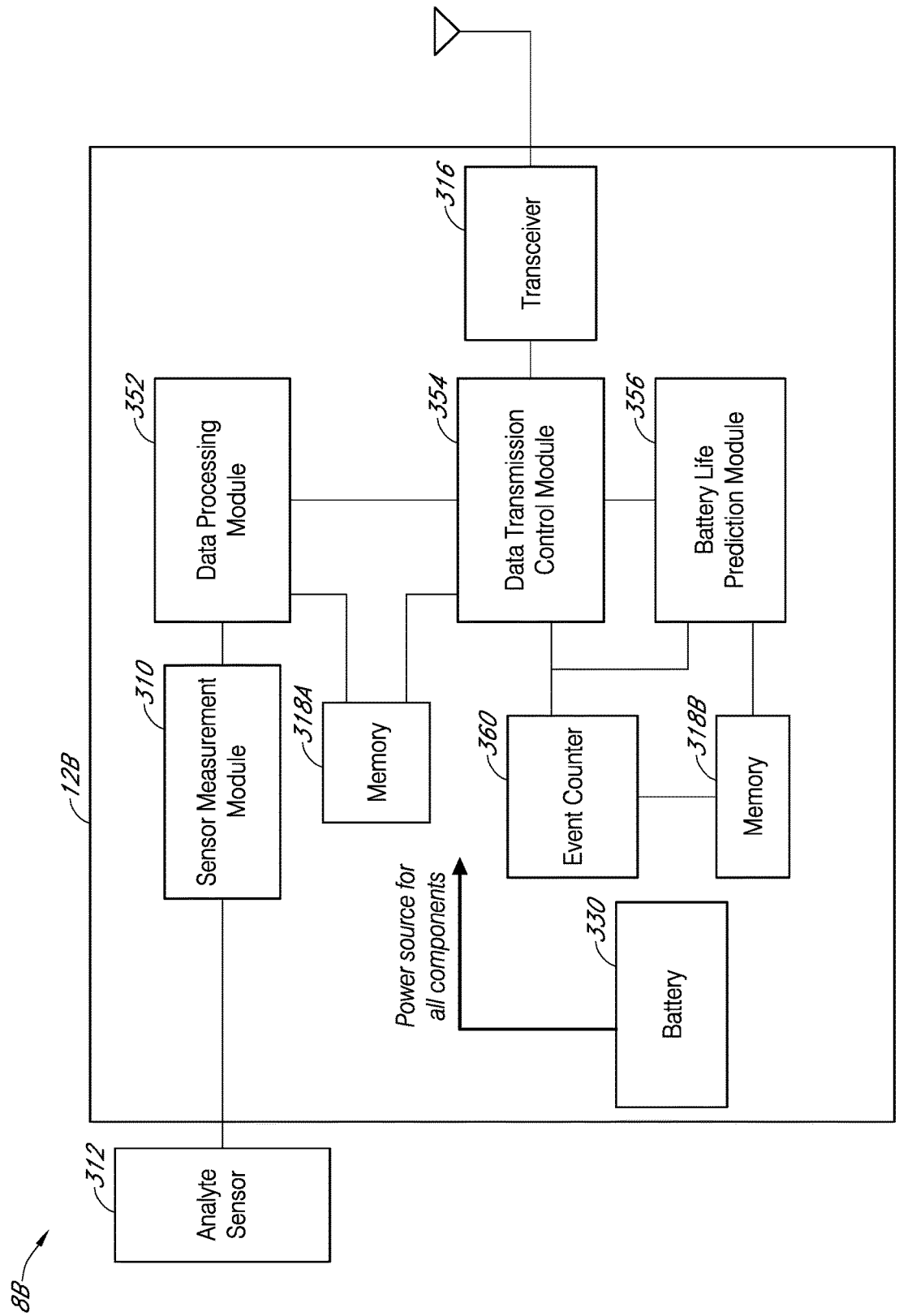
FIG. 7 is an exemplary block diagram of certain embodiments of an analyte sensor system capable of monitoring a current power level of a battery installed in the analyte sensor system and predicting remaining useful life of the battery based on counting of specific events associated with usage of the analyte sensor system according to certain aspects of the present disclosure.

The four arrangements depicted in FIGS. 6A-D include battery measurement modules 340 configured for a direct measurement of a certain parameter of the battery such as the voltage drop or load current. In some cases, the current power level of the battery can be determined by counting a number of specific events associated with usage of the analyte sensor system. FIG. 7 is an exemplary block diagram of certain embodiments of an analyte sensor system 8B capable of monitoring a current power level of a battery 330 installed in the analyte sensor system 8B and predicting remaining useful life of the battery 330 based on counting of specific events associated with usage of the analyte sensor system 8B according to certain aspects of the present disclosure.

Instead of the battery measurement module 340, the analyte sensor system 8B includes an event counter 360 configured to count a number of events associated with usage of the analyte sensor system 8B. In some embodiments, the event counter 360 can be configured to increment the number of events based on number and type of transactions performed by the analyte sensor system 8B. For example, different transactions may be assigned different increment numbers commensurate with the power drawn from the battery to complete the transactions. By way of illustration, each regularly-scheduled transmission of an analyte value may be assigned an increment number of 1 while each bulk-transfer of stored past analyte values may be assigned an increment number of 10. The data transmission control module 354 can send a signal indicating the occurrence and type of each transaction and the event counter 360 can increment the number of events based on the type of each transaction. The event counter 360 thus provides an output that is indicative of a total amount of power drawn from the battery 330 so far and hence indicative a current (remaining) power level of the battery 330.

In some embodiments, the event counter 360 is further configured to increment the number of events based on time elapsed since the battery was first installed in the analyte sensor system, including both when the analyte sensor system is in a low-power shelf (or storage) mode and in normal operational mode. Thus, even if the analyte sensor system 8B was sitting on a shelf before first usage, the event counter 360 can be configured to increment at predetermined time intervals associated with the sensor being in storage mode. This time-based increment scheme takes into account of the fact that, even while it is inside a package on the shelf, the analyte sensor system 8B is using power from the battery 330 for tasks such as checking an electrical contact to determine whether the analyte sensor system 8B has been removed from the package. Even if such a task consumes a very small amount of power each time, it can have a size impact on the power level of battery if the analyte sensor system 8B has been on the shelf for an extended amount of time. The time-based increment scheme can, therefore, provide a more accurate accounting of a current power level of the battery.

The analyte sensor systems 8A, 8B of FIGS. 5 and 7 include the battery life prediction module 356 configured to predict remaining useful life of the battery based on the measured value indicative of the current power level of the battery 330 (e.g., voltage drop, Coulomb count and/or event count) and optionally also on assumed future usage of the analyte sensor system. In those embodiments of the analyte sensor system 8A of FIG. 5 configured to measure the battery's voltage drop as an indication of the battery's current power level (e.g., the embodiments employing the arrangements of FIGS. 6A-6C), the battery life prediction module 356 can predict the remaining useful life of the battery 330 by determining when the voltage drop will exceed a predefined maximum allowed voltage drop. In those embodiments of the analyte sensor system 8B of FIG. 7 configured to count the number of transactions, the battery life prediction module 356 can be configured to predict the remaining useful life of the battery 330 by determining when the number of transactions will exceed a predefined maximum allowed number of transactions. In those embodiments where the prediction of the remaining useful life of the battery 330 is also based on assumed future usage of the analyte sensor system, the assumed future usage can be determined based on history of prior usage stored in the memory 318B. For example, the memory 318B can store data indicating the number and type of data transmission events over a predefined number of past update cycles. Based on such data, the battery life prediction module 356 can calculate the expected frequencies of different types of transmission events and use the calculated frequencies as the basis for determining the assumed future usage.

In certain embodiments, the data transmission control module 354 is configured to control one or more data transmission functions of the analyte sensor system 8A, 8B based on the measured value indicative of the current power level of the battery 330 and/or the predicted remaining useful life of the battery 330. For example, the data transmission control module 354 can be configured to disable or modify one or more data transmission functions of the analyte sensor system 8A, 8B if the current power level of the battery 330 falls below a critical threshold value (e.g., the measured voltage drop at a nominal load current is greater than 1.9V) and/or the predicted remaining useful life of the battery is less than a critical predefined time (e.g., less than one hour). Such disabled or modified data transmission functions can include extending or skipping some or all regularly-scheduled transmissions of analyte values and/or a bulk transfer of stored past measured analyte values.

In certain embodiments, the data transmission control module 354 is configured to cause the transceiver 316 to transmit data indicative of the current power level of the battery 330 and/or the predicted remaining useful life of the battery 330 to the display device 110, 120, 130, 140 (FIGS. 1 and 3). The display device 110, 120, 130, 140 can be configured to display such battery-related data received from the transceiver 316 along with the analyte values. In some embodiments, the data transmission control module 354 is configured to cause the transceiver 316 to transmit to the display device 110, 120, 130, 140 an alert indicating that the current power level of the battery is less than a predefined power level and/or the predicted remaining useful life of the battery is less than a predefined time. The display device 110, 120, 130, 140 can be configured to provide such an alert to the user via a visual or an audio alarm. In certain embodiments, the display device 110, 120, 130, 140 is configured to provide a first notification indicative of the predicted remaining useful life of the battery to the user. In some of such embodiments, the display device can be configured to provide, after the predicted remaining useful life of the battery, a second notification indicating that one or more functions of the analyte sensor system, such as a bulk transfer of stored past measured analyte values and/or regularly regularly-scheduled transmissions of analyte values, have been disabled.

It shall be appreciated that some or all of the features of the data processing module 352, data transmission control module 354, battery life prediction module 356 and event counter 360 described above with respect to FIGS. 5 and 7 may be implemented in and/or performed by hardware, software, firmware, or any combination thereof incorporated into one or more of computing devices, such as the processor/microcontroller 314 of the analyte sensor system 8 depicted in FIG. 3.

Figure 8:
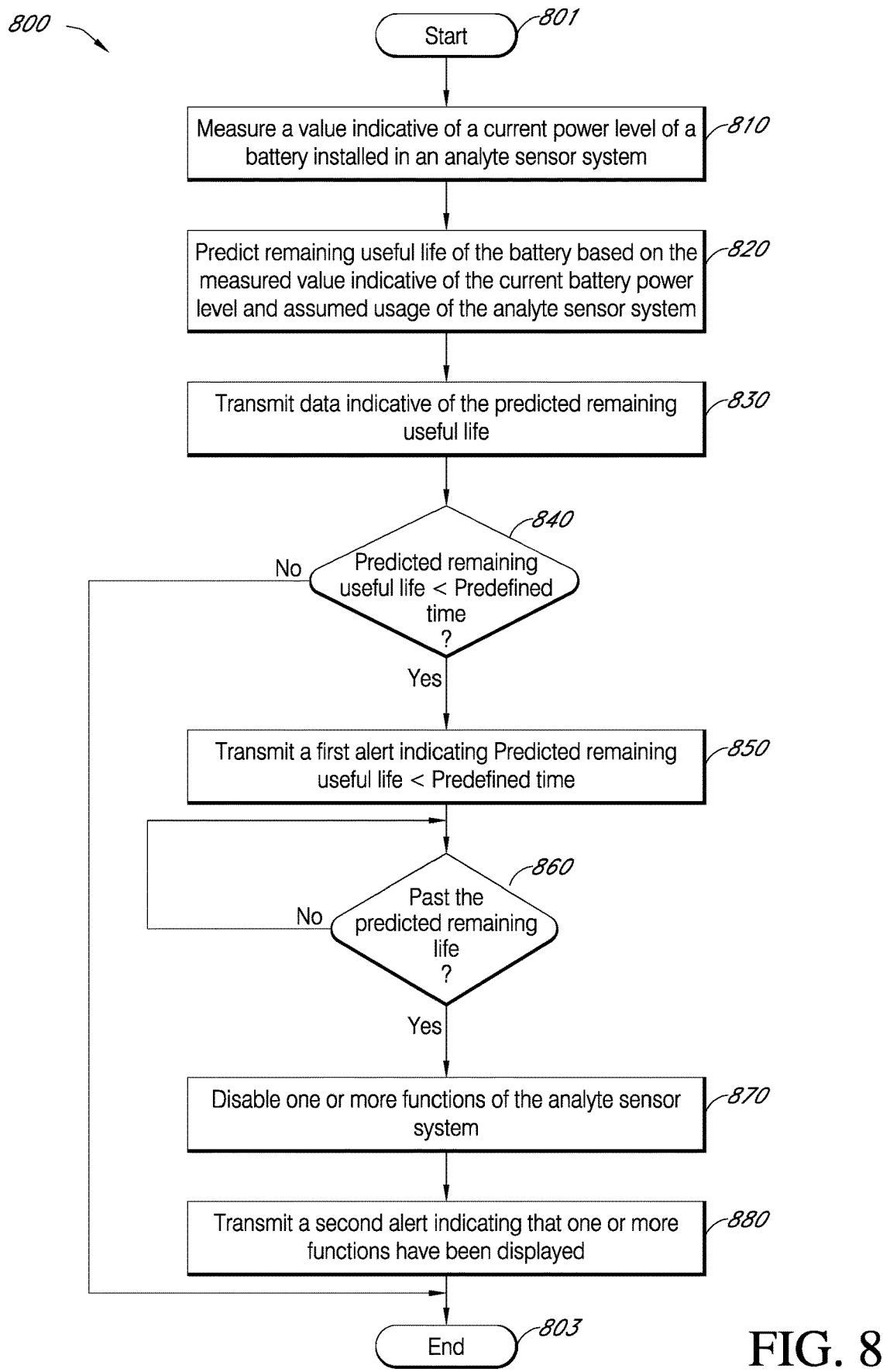
FIG. 8 is a flowchart illustrating an exemplary process for monitoring a battery installed in an analyte sensor system worn by a user according certain aspects of the present disclosure.

FIG. 8 is a flowchart illustrating an exemplary process 800 for monitoring a battery installed in an analyte sensor system worn by a user according certain aspects of the present disclosure. For ease of illustration only without any intent to limit the scope of the present disclosure in any way, the exemplary process 800 will be described with reference to the exemplary analyte sensor system embodiments depicted in FIGS. 5, 6A, 6B, 6C, 6D and 7. Those skilled in the art shall readily appreciate that the exemplary process 800 described herein can be implemented with a variety of components, processors and modules, non-limiting examples of which are shown in the exemplary analyte sensor system embodiments depicted in FIGS. 3, 5, 6A, 6B, 6C, 6D and 7. The exemplary battery monitoring process 800 can be initiated at a predefined frequency, such as after a predetermined number of update cycles (e.g., between about 20 and 50 update cycles) or after occurrence of a specific event, such as a new sensor initiation or a file transfer.

The process 800 begins at start state 801 and proceeds to operation 810 where a value indicative of a current power level of the battery 330 is measured. As described above with respect to FIGS. 6A, 6B and 6C, the measured value can be a voltage drop indicative of the internal resistance of the battery 330. In some embodiments, the measured voltage drop is compared to a predetermined voltage profile curve associated with the battery 330 determine the battery's current power level to determine the current power level. As described with respect to FIGS. 6A and 6B, the voltage drop can be measured while the battery is connected to an artificial load such a passive component (e.g., capacitor and/or resistor) or an active hardware such as a constant current source (based on an operational amplifier or a MOSFET). As described with respect to FIG. 6C, the voltage drop can be also measured while the analyte sensor system 8A, 8B performs one or more tasks known to draw a constant current from the battery 330. Such tasks can include a specific wireless transmission mode of the transceiver 316. As described with respect to FIG. 6D, the measured value indicative of the current power level of the battery 330 can be an output of a Coulomb counter configured to provide an integral of a load current drawn from the battery 330 over time.

As described with respect to FIG. 7, the measured value indicative of the current power level of the battery 330 can be a number of event counts associated with usage of the analyte sensor system 8A, 8B. The number of event counts can be incremented based on number and/or type of transactions performed by the analyte sensor system 8A, 8B. The transactions can include regularly-scheduled transmissions of a current measured analyte value and a bulk transfer of stored past measured analyte values. Each bulk transfer, which typically consumes a greater amount of battery power than each regularly-scheduled transmission, can cause a greater increment in the number of events compared to the regularly-scheduled transmission. In some embodiments, the number of event counts includes a number of time counts indicative of time elapsed since the battery was installed in the analyte sensor system 8A, 8B. The elapsed time can include time the analyte sensor system 8A, 8B was on a shelf prior to first usage.

The process 800 proceeds to operation 820 where the battery life prediction module 356 predicts remaining useful life of the battery 330 based on the measured value indicative of the current power level of the battery 330 and assumed future usage of the analyte sensor system 8A, 8B. The assumed future usage can be determined based on stored history of prior usage of the analyte sensor system such the number and type of data transmission events over a predefined number of past update cycles. Based on such historical data, the battery life prediction module 356 can calculate the expected frequencies of different types of transmission events and use the calculated frequencies as the basis for determining the assumed future usage such as the expected number of regularly-scheduled transmissions and the expected number of bulk-transfers. Based on the measured value indicative of the current power level and the assumed future usage, the battery life prediction module 356 can determine how long it would take the battery's power level to fall below a minimum power level required for operation of the analyte sensor system 8A, 8B.

The process 800 proceeds to operation 830 where the data transmission control module 354 causes the transceiver 316 to transmit data indicative of the predicted remaining useful life of the battery 330 to the display device 110, 120, 130, 140. In some embodiments, the data transmission control module 354 is configured to transmit data indicative of the current power level of the battery 330 in addition to or in lieu of the data indicative of the predicted remaining useful life of the battery 330. In some embodiments, the display device 110, 120, 130, 140 can be configured to display the data indicative of the current power level and/or the predicted remaining useful life of the battery received from the transceiver 316.

The process 800 proceeds to query state 840 where it is determined whether the predicted remaining useful life of the battery 330 is below a predefined time. In some embodiments, the predefined time is between about 2 to 4 weeks. If it is determined at the query state 840 that the predicted remaining useful life is not below the predefined time (No), the process 800 ends at end state 803 and a next battery monitoring process 800 can be initiated after a predefined number of update cycles as described above. On the other hand, if it is determined at the query state 840 that the predicted remaining useful life is below the predefined time (Yes), the process 800 proceeds to operation 850 where the data transmission control module 354 causes the transceiver 316 to transmit a first alert indicating that the predicted remaining useful life has fallen below the predetermined time to the display device 110, 120, 130, 140 or that there is only a predetermined time (e.g., 3 weeks) of useful life left in the battery. Upon reception of the first alert, the display device 110, 120, 130, 140 can provide a visual or audio notification to the user indicating the predicted remaining useful battery life. Such a notification can allow the user to plan ahead and order a new analyte sensor system or replace the battery in the existing analyte sensor system. In some embodiments, the display device 110, 120, 130, 140 can provide a gas gauge-type of display that indicates the current battery power level and/or the predicted remaining battery life (e.g., in days). The display device can also provide a data transfer gauge that display how many more times a user can perform a bulk transfer operation.

The process 800 proceeds to query state 860 where it is determined whether the predicted remaining useful life of the battery has been past. This determination can involve keeping track of time elapsed since the above-described determination at the query state 840 and comparing the elapsed time to the predicted remaining useful life. If it is determined that the predicted remaining useful life has not been exceeded (No), the process 800 loops back to the query state 860 and waits for the query condition (i.e., time passage of the predicted remaining useful life) to be satisfied. On the other hand, if it is determined that the predicted remaining useful life has been exceeded (Yes), the process 800 proceeds to operation 870 where the data transmission control module 354 disables one or more functions of the analyte sensor system 8A, 8B and to operation 880 where the data transmission control module 354 causes the transceiver 316 to transmit a second alert to the display device 110, 120, 130, 140 indicating that the one or more functions have been disabled or modified to conserve power. In some embodiments, the one or more disabled or modified functions include a bulk transfer of stored past measured analyte values and/or regularly-scheduled transmissions of analyte values.

Figure 9:
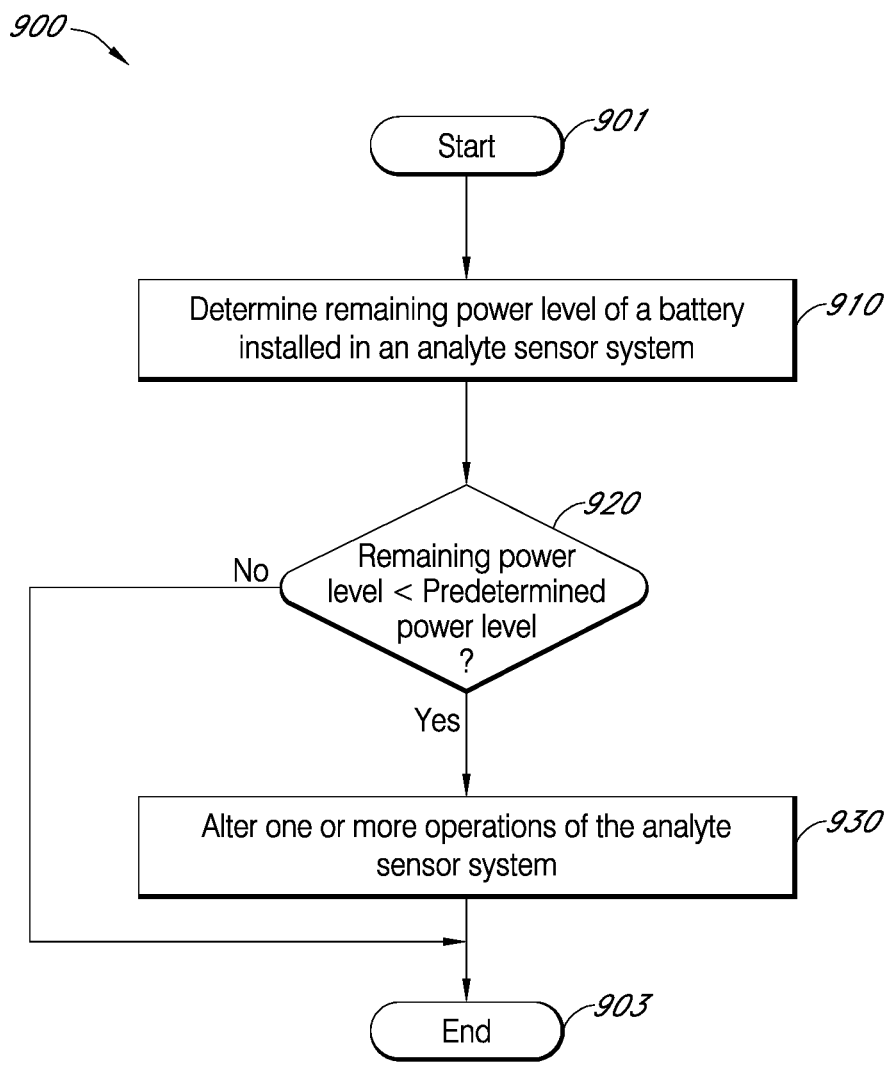
FIG. 9 is a flowchart illustrating an exemplary process for prolonging life of a battery installed in an analyte sensor system worn by a user according certain aspects of the present disclosure.

In certain embodiments of the present disclosure, the analyte sensor system 8A, 8B can take some proactive actions in order to prolong the useful life of the battery 330. For example, when the battery's remaining power level falls below a predetermined power level, one or more functions of the analyte sensor system 8A, 8B can be altered in ways that consume less battery power. FIG. 9 is a flowchart illustrating an exemplary process 900 for prolonging life of a battery installed in an analyte sensor system worn by a user according certain aspects of the present disclosure. For ease of illustration only without any intent to limit the scope of the present disclosure in any way, the exemplary process 900 will be described with reference to the exemplary analyte sensor system embodiments depicted in FIGS. 5, 6A, 6B, 6C, 6D and 7. Those skilled in the art shall readily appreciate that the exemplary process 900 described herein can be implemented with a variety of components, processors and modules, non-limiting examples of which are shown in the exemplary analyte sensor system embodiments depicted in FIGS. 3, 5, 6A, 6B, 6C, 6D and 7. The exemplary battery monitoring process 900 can be initiated at a predefined frequency, such as after a predetermined number of update cycles (e.g., between about 20 and 50 update cycles) or after occurrence of a specific event, such as a new sensor initiation or a file transfer.

The process 900 begins at start state 901 and proceeds to operation 910 where a remaining power level of the battery 330 is determined. In some embodiments, the operation 910 involves the battery measurement module 340 measuring a value indicative of a current power level of the battery, such as a voltage drop at a certain load current, a Coulomb count and an event count as described above with respect to FIGS. 6A, 6B, 6C, 6D, and determining the remaining power level based on the measured parameter. In some embodiments, the operation 910 involves the battery life prediction module 356 predicting the remaining useful life of the battery based on the measured value and assumed future usage of the analyte system 8A, 8B described above with respect to FIGS. 5 and 7.

The process 900 proceeds to query state 920 where it is determined whether the remaining power level of the battery 330 is less than a predetermined power level. In some embodiments, this determination involves the data transmission control module 354 comparing the measured value indicative of a current power level of the battery (e.g., a measured voltage drop) to a predetermined value (e.g., a threshold voltage drop). In other embodiments, this determination involves the data transmission control module 354 comparing the predicted remaining useful life to a predetermined time. If it is determined at the query state 920 that the remaining power level is not less than the predetermined power level (No), the process 900 ends at end state 903. On the other hand, if it is determined at the query state 920 that the remaining power level is less than the predetermined power level (Yes), the process 900 proceeds to operation 930 where one or more operations of the analyte sensor system 8A, 8B are altered.

The altering operation or step 930 can include the data transmission control module 354 changing (e.g., modifying, adding, removing, and/or cancelling) one or more data transmission operations performed by the analyte sensor system 8A, 8B. In certain embodiments, the data transmission control module 354 can cause a reduction in the power level of radio frequency transmissions by the transceiver 316. The radio frequency transmission power level can be reduced upon a prior determination that the analyte sensor system 8A, 8B is in close proximity of the display device 110, 120, 130, 140 based on, for example, a measured RSSI (Received Signal Strength Indication). In some embodiments, the analyte sensor system 8A, 8B can be configured to save battery power by varying the transmission power level based on RSSI values without monitoring the battery power to save power consumption. In some embodiments, the altering operation or step 930 can include the data transmission control module 354 changing bulk transfer operations for transmitting stored past measured analyte values. In some of such embodiments, the bulk transfer operations are cancelled altogether. In others, only part of the stored past measured analyte values are included in the bulk transfers. In certain embodiments, the altering operation or step 930 can include the data transmission control module 354 increasing an interval (e.g., $T_{interval}$) between regularly-scheduled transmissions of analyte values. The interval can vary from 1 minute to 15 minutes, for example. In some embodiments, altering operation or step 930 can include the data transmission control module 354 causing the transceiver 316 to skip one or more of regularly-scheduled transmissions of analyte values. For example, every other $T_{interval}$=5 minute transmission can be skipped so that the analyte sensor system 8A, 8B only transmits every 10 minutes. In some embodiments, the altering operation or step 930 includes the data transmission control module 354 cancelling regularly-scheduled transmissions of analyte values and transmitting an analyte value in response to one or more events instead. In some of such embodiments, the one or more events that trigger the transmission of an analyte value include a user prompt of the analyte value received from the display device 110, 120, 130, 140. In some embodiments, the one of more events that trigger the transmission of an analyte value include one or more analyte values (e.g., glucose values) exceeding or falling below a threshold analyte value.

Figure 10:
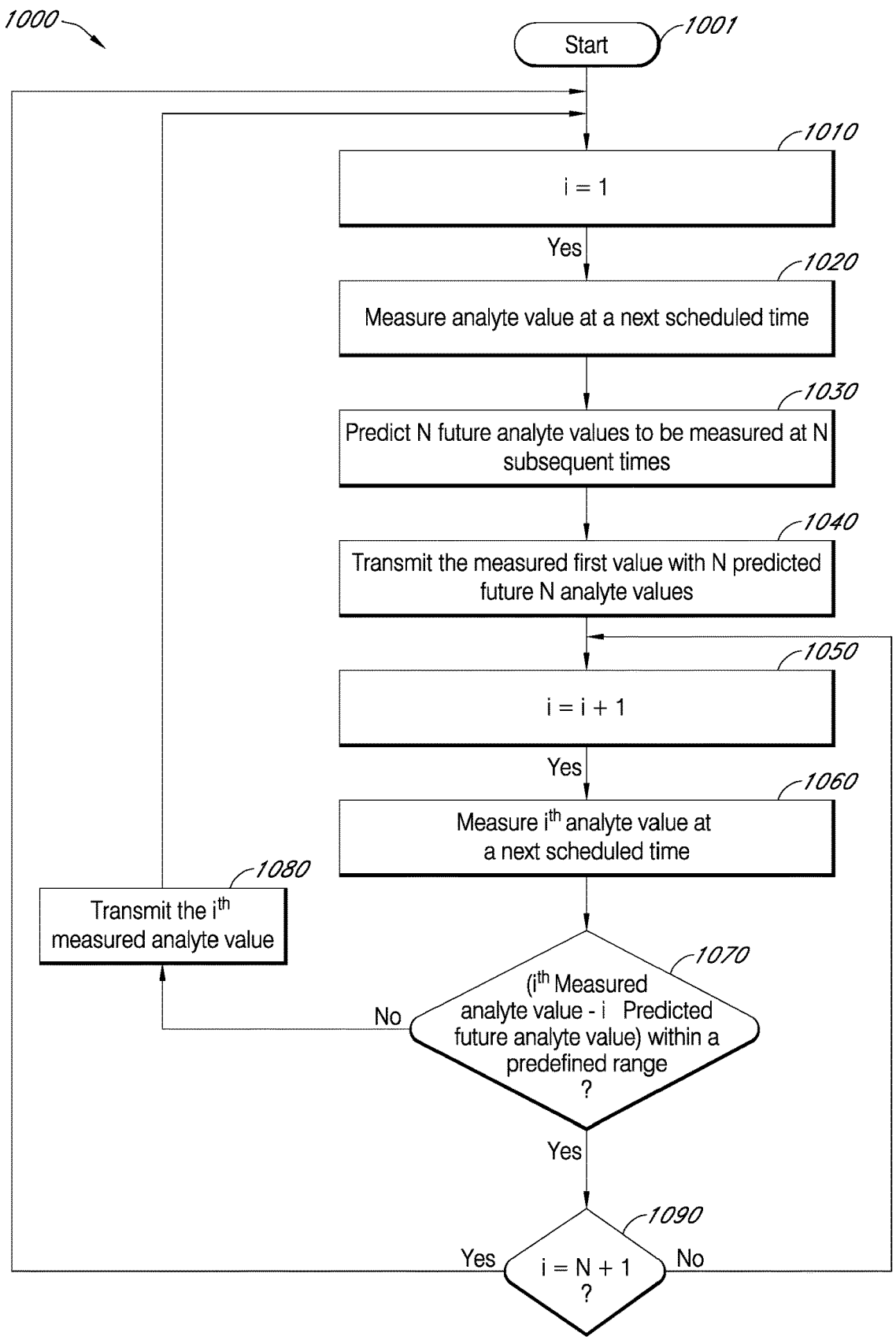
FIG. 10 is a flowchart illustrating an exemplary process for prolonging life of a battery installed in an analyte sensor system worn by a user according certain aspects of the present disclosure.

In certain embodiments of the present disclosure, the battery life can be prolonged by reducing the number of regularly-scheduled transmissions of analyte values. This can be achieved, for example, by transmitting one or more predicted future analyte values along with the current measured analyte value and skipping one or more subsequently-scheduled transmissions of the measured future analyte values if those measured values are within a predefined range of the already-sent future predicted analyte values. When the analyte values (e.g., glucose values) do not vary from samples to samples under normal conditions, this scheme can result in a significant reduction in the number of regularly-scheduled transmissions and attendant battery power savings. FIG. 10 is a flowchart illustrating an exemplary process 1000 for prolonging life of a battery installed in an analyte sensor system worn by a user according certain aspects of the present disclosure. For ease of illustration only without any intent to limit the scope of the present disclosure in any way, the exemplary process 1000 will be described with reference to the exemplary analyte sensor system embodiments depicted in FIGS. 5, 6A, 6B, 6C, 6D and 7. Those skilled in the art shall readily appreciate that the exemplary process 1000 described herein can be implemented with a variety of components, processors and modules, non-limiting examples of which are shown in the exemplary analyte sensor system embodiments depicted in FIGS. 3, 5, 6A, 6B, 6C, 6D and 7.

The process 1000 starts at start state 1001 and proceeds to operation 1010 where time index i is initialized to 1. The process 1000 proceeds to operation 1020 where the sensor measurement module 310 measures a first analyte value at a first scheduled time (e.g., $T_1$). The process 1000 proceeds to operation 1030 where N future analyte values to be measured at N future scheduled measurement times (e.g., $T_2$, $T_3$, ..., $T_{N+1}$) are predicted. In some embodiments, N is 1. In other embodiments, N is a positive integer between 2 and 5. The prediction operation 1030 can include the data processing module 352 predicting the N future analyte values based on past measured analyte values. For example, the data processing module 352 can fit a line through a predetermined number of past measured analyte values using, for example, a linear or least squares method and predict the N future analyte values based on an equation for the fitted line.

The process 1000 proceeds to operation 1040 where the data transmission control module 354 causes the transceiver 316 to transmit the measured first analyte value along with the N predicted future analyte values. The process 1000 proceeds to operation 1040 where the time index i is incremented by 1 and then to operation 1060 where the next (e.g., second) analyte value is measured at a next scheduled measurement time (e.g., $T_2$). The process 1000 proceeds to query state 1070 where it is determined whether a difference between the measured second analyte value and the predicted second analyte value is within a predefined range. In some embodiments, the predefined range can be a percentage difference, such as between 1 and 5% of the predicted or measured second analyte value, or a numerical difference, such as the predicted and measured analyte values being no more than 10 mg/dL different.

In certain embodiments, the predefined range is variable depending on at least one of a current analyte value and a predicted analyte value. For example, in the case of continuous glucose sensing, the predefined range can also vary depending upon the current glucose value and/or the predicted glucose value. For example, the predefined range may be smaller when the glucose value is in a clinical risky zone because a small difference may have more clinical impact. To illustrate, if the glucose value is 70, then a small difference of 5 or 10 mg/dL between the predicted and actual glucose value is clinically significant. In contrast, if the glucose value is 130, and 5 or 10 mg/dL difference is not nearly as clinically significant. In some implementations, the predefined range can be smaller for low glucose values and higher for high glucose values. In addition, in some embodiments, the variable predefined range can be determined based at least partly on a clinical error grid associated with the analyte (e.g., glucose) being measured, such as the Clarke-Error grid.

If the difference between the measured second analyte value and the predicted second analyte value is outside the predetermined range (No), the process 1000 proceeds to operation 1080 where the data transmission control module 354 causes the transceiver 316 to transmit the measured second analyte value at a next scheduled transmission time. The operation 1000 then loops back to the operation 1010 where the time index i is re-initialized to 1 and the process 1000 repeats. In some embodiments, the data transmission control module 354 causes the transceiver 316 to transmit the measured second analyte value along with another set of N future analyte values determined by the data processing module 352 based on past measured analyte values.

On the other hand, if the difference between the measured second analyte value and the predicted second analyte value is within the predefined range (Yes), the process 1000 proceeds to query state 1090 where it is determined whether the time index i is equal to N+1, that is, whether all N future analyte values have been measured and compared to the N predicted future analyte values. If this condition is not met (Yes), the process 1000 loops back to the operation 1010 where the time index i is re-initialized to 1 and the process 1000 repeats.

On the other hand, if the time index i is not equal to N+1, meaning that not all N future analyte values have been measured and compared to the N predicted future analyte values, the process 1000 loops back to the operation 1050 where the time index i is incremented by 1 and then to the operation 1060 where the next (e.g., third) analyte value is measured at a next scheduled measurement time (e.g., $T_3$) and then to the query state 1070 where it is determined whether a difference between the measured third analyte value and the predicted third analyte value is within a predefined range. If the answer to the query state 1070 is No, the process 1000 proceeds to the operation 1080 where the data transmission control module 354 causes the transceiver 316 to transmit the measured third analyte value at a next scheduled transmission time. The operation 1000 then loops back to the operation 1010.

On the other hand, if the answer to the query state 1070 is Yes (i.e., the difference is within the predefined range), the process 1000 proceeds to the query state 1090 where it is determined whether all N future analyte values have been measured and compared to the N predicted future analyte values. If the answer to the query state 1090 is Yes, the process 1000 loops back to the operation 1010 where the time index i is re-initialized to 1 and the process 1000 repeats. On the other hand, if the answer to the query state 1090 is No, the process 1000 loops back to the operation 1050 and then to the subsequent operations and query states until either the difference between the $i^{th}$ measured analyte value and the ith predicted future analyte value is outside the predefine range or when all N future analyte values have been measured and compared to the N predicted future analyte values.

Various implementations of the subject matter described herein may be realized in digital electronic circuitry, integrated circuitry, specially designed ASICs (application specific integrated circuits), computer hardware, firmware, software, and/or combinations thereof. The circuitry may be affixed to a printed circuit board (PCB), or the like, and may take a variety of forms, as noted. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, or code) include machine instructions for a programmable processor, and may be implemented in a high-level procedural and/or object-oriented programming language, and/or in assembly/machine language. As used herein, the term "machine-readable medium" refers to any non-transitory computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. An analyte sensor system, comprising:
   an analyte sensor; and
   sensor electronics circuitry electrically coupled to the analyte sensor, the sensor electronics circuitry comprising:
   a transceiver configured to transmit and receive wireless signals;
   a power source; and
   at least one processor coupled to the transceiver and to a memory, the at least one processor being configured to:
   determine a resistance associated with the power source, based at least in part on a known current of the power source, wherein the known current of the power source is associated with analyte transmission;
   determine whether the resistance associated with the power source is above a predefined resistance value; and
   in response to determining the resistance associated with the power source is above the predefined resistance value, cause a change in one or more data transmission operations of the transceiver of the sensor electronics circuitry.

2. The analyte sensor system of claim 1, wherein the resistance associated with the power source is an internal resistance.

3. The analyte sensor system of claim 1, the at least one processor being further configured to:
   determine a remaining useful life of the power source based on the resistance associated with the power source and a predicted future usage of the analyte sensor system.

4. The analyte sensor system of claim 1, wherein the resistance associated with the power source is determined further based on an artificial load.

5. The analyte sensor system of claim 4, wherein the artificial load is a passive load.

6. The analyte sensor system of claim 4, wherein the artificial load is an active load.

7. The analyte sensor system of claim 1, wherein the resistance associated with the power source is associated with a current power level of the power source.

8. A method comprising:
   determining a resistance associated with a power source of sensor electronics circuitry, based at least in part on a known current of the power source, wherein the known current of the power source is associated with analyte transmission;
   determining whether the resistance associated with the power source is above a predefined resistance value; and
   in response to determining the resistance associated with the power source is above the predefined resistance value, causing a change in one or more data transmission operations of a transceiver of the sensor electronics circuitry.

9. The method of claim 8, wherein the resistance associated with the power source is an internal resistance.

10. The method of claim 8, further comprising determining a remaining useful life of the power source based on the resistance associated with the power source and a predicted future usage of an analyte sensor system comprising the sensor electronics circuitry.

11. The method of claim 8, wherein the resistance associated with the power source is determined further based on an artificial load.

12. The method of claim 11, wherein the artificial load is a passive load.

13. The method of claim 11, wherein the artificial load is an active load.

14. The method of claim 8, wherein the resistance associated with the power source is associated with a current power level of the power source.

15. A non-transitory computer-readable medium storing computer-executable instructions, which, when executed by one or more processors of an analyte sensor system, perform an operation comprising:
   determining a resistance associated with a power source of sensor electronics circuitry, based at least in part on a known current of the power source, wherein the known current of the power source is associated with analyte transmission;

determining whether the resistance associated with the power source is above a predefined resistance value; and in response to determining the resistance associated with the power source is above the predefined resistance value, causing a change in one or more data transmission operations of a transceiver of the sensor electronics circuitry.

16. The non-transitory computer-readable medium of claim 15, wherein the resistance associated with the power source is an internal resistance.

17. The non-transitory computer-readable medium of claim 15, the operation further comprising determining a remaining useful life of the power source based on the resistance associated with the power source and a predicted future usage of the analyte sensor system.

18. The non-transitory computer-readable medium of claim 15, wherein the resistance associated with the power source is determined further based on an artificial load.

19. The non-transitory computer-readable medium of claim 18, wherein the artificial load is a passive load.

20. The non-transitory computer-readable medium of claim 18, wherein the artificial load is an active load.

* * * * *